(12) United States Patent
Araki et al.

(10) Patent No.: US 7,214,470 B2
(45) Date of Patent: May 8, 2007

(54) FLUORINE-CONTAINING ETHYLENIC MONOMER HAVING HYDROXYL GROUP OR FLUOROALKYL CARBONYL GROUP AND FLUORINE-CONTAINING POLYMER PREPARED BY POLYMERIZATION OF SAME

(75) Inventors: Takayuki Araki, Settsu (JP); Yuzo Komatsu, Settsu (JP); Meiten Koh, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 331 days.

(21) Appl. No.: 10/644,953

(22) Filed: Aug. 21, 2003

(65) Prior Publication Data

US 2004/0002575 A1   Jan. 1, 2004

Related U.S. Application Data

(63) Continuation-in-part of application No. PCT/JP02/01518, filed on Feb. 21, 2002.

(30) Foreign Application Priority Data

Feb. 23, 2001 (JP) .............................. 2001-049248
Feb. 23, 2001 (JP) .............................. 2001-049249

(51) Int. Cl.
   *G03F 7/038* (2006.01)
(52) U.S. Cl. .............................. 430/276.1; 430/270.1; 526/242; 526/244; 526/247
(58) Field of Classification Search ............. 430/276.1, 430/270.1; 526/244, 247, 242
   See application file for complete search history.

(56) References Cited

U.S. PATENT DOCUMENTS

| | | | |
|---|---|---|---|
| 3,362,985 A | | 1/1968 | Gilbert et al. |
| 3,391,119 A | * | 7/1968 | Anderson ................... 526/244 |
| 3,414,549 A | * | 12/1968 | Schaefgen ................... 526/242 |
| 3,444,148 A | * | 5/1969 | Adelman ..................... 526/242 |
| 5,986,150 A | * | 11/1999 | Araki et al. ................. 568/843 |
| 6,610,456 B2 | * | 8/2003 | Allen et al. ............... 430/270.1 |

FOREIGN PATENT DOCUMENTS

| | | | |
|---|---|---|---|
| EP | 1375598 A1 | * | 1/2004 |
| EP | 1498459 A1 | * | 1/2005 |
| JP | 55-102629 | | 8/1980 |
| JP | 5-238988 | | 9/1993 |
| JP | 05-238988 A | * | 9/1993 |
| JP | 2002-90996 | | 3/2002 |
| JP | 2002/090996 A | * | 3/2002 |
| JP | 2002-90996 A | * | 3/2002 |
| WO | WO 00/67072 A | | 11/2000 |

OTHER PUBLICATIONS

International Preliminary Examination Report for PCT/JP/01518 (Japanese language).
International Search Report for PCT/JP/01518 dated Jun. 4, 2002.
English language translation of International Preliminary Examination Report for PCT/JP02/01518 dated Mar. 4, 2003.
M. Nakamura et al.; "Liquid Separation with Fluorinated Polymer Membranes"; Journal of Membrane Science, vol. 36, Mar. 1988, pp. 343-351.
Patent Abstracts of Japan; vol. 012, No. 037, Feb. 4, 1988 & JP 62 186907 A (Agency of Ind Science & Technol), Aug. 15, 1987.
Database WPI, Section Ch, Week 198444, Derwent Publications Ltd., London, GB; Class E16, AN 1984-272818, XP002352524 & JP 59 167533 A (Asahi Glass Co Ltd) Sep. 21, 1984.
Konrad Von Werner et al.; "The Synthesis and Some Reactions of Pentafluoroethyl Vinyl Ketone"; Journal of Fluorine Chemistry, vol. 10, 1977, pp. 387-394, XP-002351940.
B.C. Anderson; "A Synthesis of Perfluoroalkyl Trifluorovinyl Ketones"; The Journal of Organic Chemistry, vol. 33, No. 3, Mar. 1968, pp. 1016-1018, XP-002351941.
M. Tordeux et al.; "Synthese de la Trifluoromethyl-vinyl-cetone"; Journal of Fluorine Chemistry, vol. 20, 1982, pp. 301-306, XP-002351942.

\* cited by examiner

*Primary Examiner*—David W. Wu
*Assistant Examiner*—Henry S. Hu
(74) *Attorney, Agent, or Firm*—Sughrue Mion, PLLC

(57) ABSTRACT

There are provided a fluorine-containing ethylenic monomer having hydroxyl group or fluoroalkyl carbonyl group and represented by the formula (1):

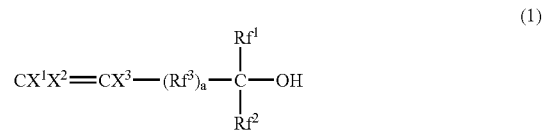

and the formula (14):

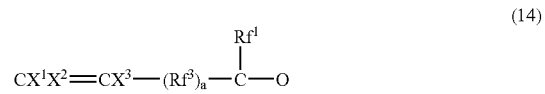

respectively, wherein $X^1$ and $X^2$ are the same or different and each is H or F; $X^3$ is H, F, Cl or $CF_3$; $Rf^1$ and $Rf^2$ are the same or different and each is a perfluoroalkyl group having 1 to 20 carbon atoms; $Rf^3$ is a fluorine-containing alkylene group having 1 to 40 carbon atoms or a fluorine-containing alkylene group having ether bond which has 1 to 100 carbon atoms and the sum of carbon atom and oxygen atom of two or more; a is 0 or 1, a fluorine-containing polymer having a structural unit of the above-mentioned monomer and a composition for a photoresist. The monomer has good polymerizability, particularly radical polymerizability, and the polymer obtained by polymerizing the monomer has excellent optical characteristics and is useful as a base polymer for an antireflection film and for a composition for a resist.

8 Claims, No Drawings

FLUORINE-CONTAINING ETHYLENIC MONOMER HAVING HYDROXYL GROUP OR FLUOROALKYL CARBONYL GROUP AND FLUORINE-CONTAINING POLYMER PREPARED BY POLYMERIZATION OF SAME

CROSS-REFERENCE TO RELATED APPLICATION

This is a continuation-in-part of PCT international application No. PCT/JP02/01518 filed on Feb. 21, 2002 pending.

BACKGROUND OF THE INVENTION

The present invention relates to a novel fluorine-containing ethylenic monomer which has hydroxyl group or fluoroalkyl carbonyl group and possesses good polymerizability, particularly radical polymerizability, and further relates to a novel fluorine-containing polymer obtained by polymerization of the monomer.

The fluorine-containing ethylenic monomer having hydroxyl of the present invention is a tertiary alcohol which has a carbon-carbon double bond having good radical polymerizability and has, on another end thereof, two fluorine-containing alkyl groups and hydroxyl which are bonded to the same carbon. The monomer is a novel compound which has not been disclosed in any literatures. The fluorine-containing ethylenic monomer having hydroxyl of the present invention can be polymerized alone and also can be polymerized with other monomer, particularly fluorine-containing ethylenic monomer having no hydroxyl. Thus hydroxyl having high acidity can be introduced to a fluorine-containing polymer.

The thus obtained fluorine-containing polymer of the present invention is also a novel compound like the above-mentioned fluorine-containing ethylenic monomer having hydroxyl.

According to the present invention, affinity for and solubility in an aqueous medium, particularly an aqueous alkaline medium are enhanced as compared with fluorine-containing polymers having hydroxyl which are obtained by polymerization of conventional fluorine-containing ethylenic monomers having hydroxyl. Further as compared with the conventional fluorine-containing polymers having hydroxyl and fluorine-containing polymers having other functional group (carboxyl or the like), transparency (particularly transparency in vacuum ultraviolet region) and low refractive index which are characteristics inherent to fluorine-containing polymers can be maintained or improved.

As mentioned above, an object of the present invention is to provide a novel fluorine-containing ethylenic monomer having hydroxyl and further a novel fluorine-containing polymer which has hydroxyl and is obtained by polymerization of the monomer.

SUMMARY OF THE INVENTION

The first of the present invention relates to a fluorine-containing ethylenic monomer having hydroxyl which is represented by the formula (1):

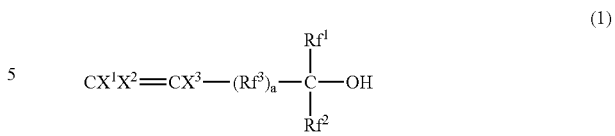

wherein $X^1$ and $X^2$ are the same or different and each is H or F; $X^3$ is H, F, Cl or $CF_3$; $Rf^1$ and $Rf^2$ are the same or different and each is a perfluoroalk group having 1 to 20 carbon atoms; $Rf^3$ is a fluorine-containing alkylene group having 1 to 40 carbon atoms or a fluorine-containing alkylene group having ether bond which has 1 to 100 carbon atoms and the sum of carbon atom and oxygen atom of two or more; a is 0 or 1.

The second of the present invention relates to a novel fluorine-containing polymer obtained by (co)polymerizing the fluorine-containing ethylenic monomer having hydroxyl of the present invention.

The third of the present invention relates to a fluorine-containing ethylenic monomer having fluoroalkyl carbonyl group which is represented by the formula (14):

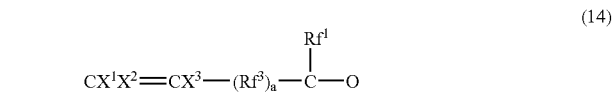

wherein $X^1$ and $X^2$ are the same or different and each is H or F; $X^3$ is H, F, Cl or $CF_3$; $Rf^1$ is a perfluoroalkyl group having 1 to 20 carbon atoms; $Rf^3$ is a fluorine-containing alkylene group having 1 to 40 carbon atoms or a fluorine-containing alkylene group having ether bond which has 1 to 100 carbon atoms and the sum of carbon atom and oxygen atom of two or more; a is 0 or 1.

The fourth of the present invention relates to a photoresist composition which is a composition comprising:

(A) a fluorine-containing polymer having, as an essential component, a structural unit obtained by polymerizing a fluorine-containing ethylenic monomer having OH group, (B) a photoacid generator, and (C) a solvent, in which, when the carbon atom bonded to OH group of the fluorine-containing ethylenic monomer having OH group is named the first carbon atom and a structure consisting of the first carbon atom up to the neighboring third or fourth carbon atom is assumed to be a model structure, the fluorine-containing ethylenic monomer having OH group satisfies Equation 1:

$$\Delta H = H(M-O^-) + 200 - H(M-OH) \leq 75 \quad \text{(Equation 1)}$$

wherein $H(M-OH)$ is a produced enthalpy of the model structure, $H(M-O^-)$ is a produced enthalpy of the fluorine-containing ethylenic monomer after dissociation of the OH group and a produced enthalpy of hydrogen ion is assumed to be a constant of 200 kJ/mol.

DETAILED DESCRIPTION

The first of the present invention relates to the fluorine-containing ethylenic monomer having hydroxyl which is represented by the formula (1):

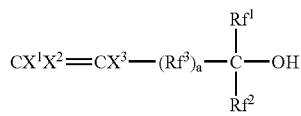

(1)

wherein $X^1$ and $X^2$ are the same or different and each is H or F; $X^3$ is H, F, Cl or $CF_3$; $Rf^1$ and $Rf^2$ are the same or different and each is a perfluoroalkyl group having 1 to 20 carbon atoms; $Rf^3$ is a fluorine-containing alkylene group having 1 to 40 carbon atoms or a fluorine-containing alkylene group having ether bond which has 1 to 100 carbon atoms and the sum of carbon atom and oxygen atom of two or more; a is 0 or 1.

Particularly preferred is a fluorine-containing ethylenic monomer having hydroxyl which is represented by the formula (2):

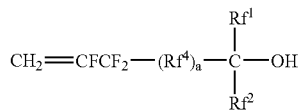

(2)

wherein $Rf^1$ and $Rf^2$ are as defined in the formula (1); $Rf^4$ is a fluorine-containing alkylene group having 1 to 39 carbon atoms or a fluorine-containing alkylene group having ether bond which has 1 to 99 carbon atoms and the sum of carbon atom and oxygen atom of two or more; a is 0 or 1, from the viewpoint of good homopolymerizability and good copolymerizability with fluorine-containing ethylenic monomer having no hydroxyl such as tetrafluoroethylene and vinylidene fluoride.

Also preferred is a fluorine-containing ethylenic monomer having hydroxyl which is represented by the formula (3):

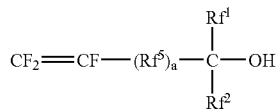

(3)

wherein $Rf^1$ and $Rf^2$ are as defined in the formula (1); $Rf^5$ is a fluorine-containing alkylene group having 1 to 40 carbon atoms or a fluorine-containing alkylene group having ether bond which has 1 to 100 carbon atoms and the sum of carbon atom and oxygen atom of two or more; a is 0 or 1, from the viewpoint of good copolymerizability with fluorine-containing ethylenic monomer having no hydroxyl such as tetrafluoroethylene and vinylidene fluoride.

In the above-mentioned formulae (1), (2) and (3), a is 0 or 1, which means that the monomers may have or may not have $Rf^3$, $Rf^4$ and $Rf^5$, respectively.

When a is 0, the monomer is concretely represented by the formula (4):

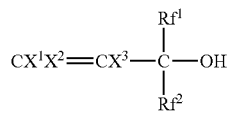

(4)

wherein $X^1$ and $X^2$ are the same or different and each is H or F; $X^3$ is H, F, Cl or $CF_3$; $Rf^1$ and $Rf^2$ are as defined in the formula (1). Examples thereof are:

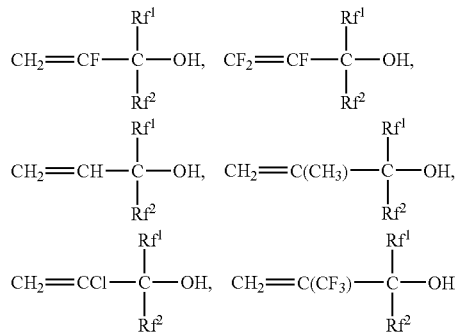

and the like.

It is particularly preferable from the viewpoint of polymerizability that at least one of $X^1$, $X^2$ and $X^3$ is H.

It is further preferable that at least one of $X^1$, $X^2$ and $X^3$ is H and $X^1$, $X^2$ and $X^3$ are not H at the same time, from the point that transparency and solubility in an aqueous alkaline solution can be improved while maintaining polymerizability. Concretely there are:

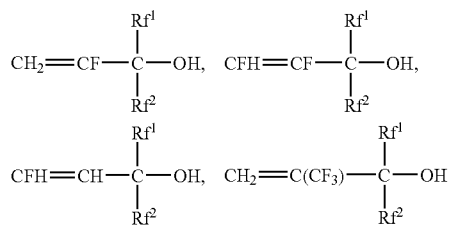

and the like.

In the formulae (1), (2) and (3), when a is 1, $Rf^3$ and $Rf^5$ are selected from a fluorine-containing alkylene group having 1 to 40 carbon atoms and a fluorine-containing alkylene group having ether bond which has 1 to 100 carbon atoms and the sum of carbon atom and oxygen atom of two or more, and $Rf^4$ is selected from a fluorine-containing alkylene group having 1 to 39 carbon atoms and a fluorine-containing alkylene group having ether bond which has 1 to 99 carbon atoms and the sum of carbon atom and oxygen atom of two or more.

Examples of the fluorine-containing alkylene groups of $Rf^3$, $Rf^4$ and $Rf^5$ are preferably:

$-(CF_2)_{n1}-$ (n1 is an integer of 1 or more),

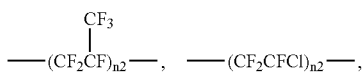

$-(CH_2CF_2)_{n2}-$, $-(CF_2CH_2)_{n2}-$ (n2 is an integer of 1 or more),

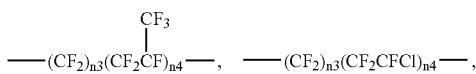

$-(CF_2)_{n3}(CH_2)_{n4}-$ (n3 and n4 are integers of 1 or more) and the like.

When $Rf^3$, $Rf^4$ and $Rf^5$ are fluorine-containing alkylene groups having ether bond, examples thereof are:

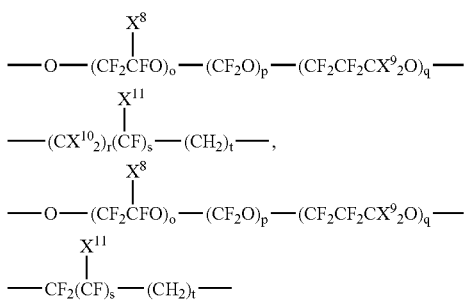

and the like, wherein $X^8$ and $X^{11}$ are the same or different and each is F or $CF_3$; $X^9$ and $X^{10}$ are the same or different and each is H or F; o+p+q is an integer of from 1 to 30; r is 0 or 1; s and t are 0 or 1.

Further in the present invention, when a is 1, examples of preferred fluorine-containing ethylenic monomer having hydroxyl are those represented by the formula (5):

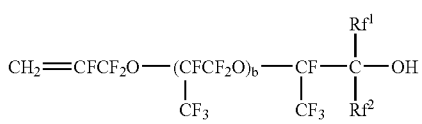

wherein $Rf^1$ and $Rf^2$ are as defined in the formula (1); b is an integer of from 1 to 13, and the formula (6):

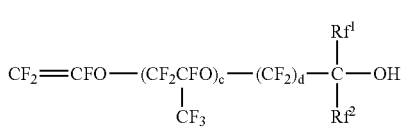

wherein $Rf^1$ and $Rf^2$ are as defined in the formula (1); c is an integer of from 1 to 13; d is an integer of from 1 to 5.

In the fluorine-containing ethylenic monomers having hydroxyl of the formulae (1), (2) and (3), a is preferably 1 from the viewpoint of solubility of the obtained polymers in an aqueous alkaline solution due to hydroxyl, transparency and low refractive index. Also for the same reason, it is preferable that $Rf^3$, $Rf^4$ and $Rf^5$ are perfluoroalkylene group and perfluoroalkylene group having ether bond in the above-mentioned examples.

In the fluorine-containing ethylenic monomers having hydroxyl of the formulae (1) to (6), $Rf^1$ and $Rf^2$ are perfluoroalkyl groups, and examples thereof are:

$F(CF_2)_{n1}$ (n1 is an integer of from 1 to 20),

(n2 is an integer of from 1 to 6) and

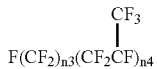

(n3 and n4 are integers which make the total number of carbon atoms of not more than 20).

Among them, preferred are $CF_3$, $C_2F_5$, $C_3F_7$, $C_4F_9$, $(CF_3)_2CF$ and the like.

In the present invention, further preferred examples of the fluorine-containing ethylenic monomers having hydroxyl are:

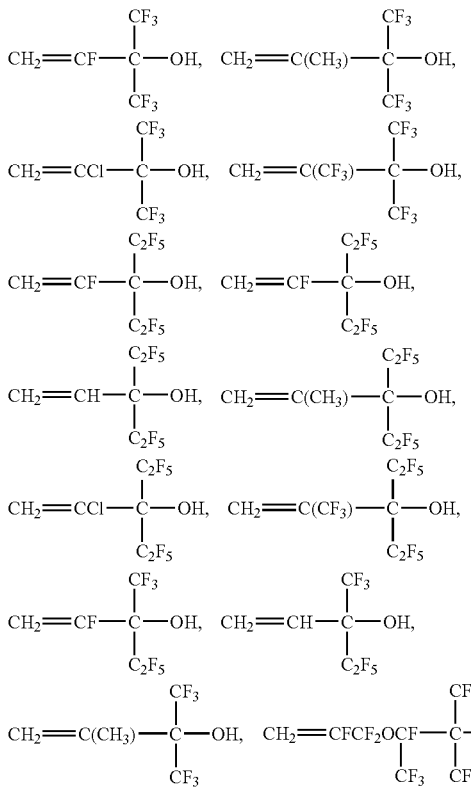

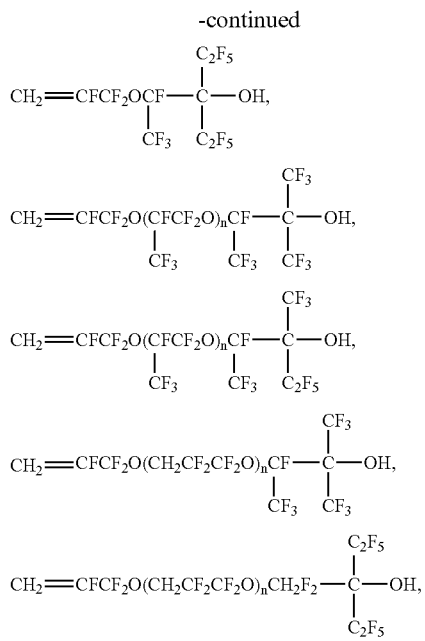

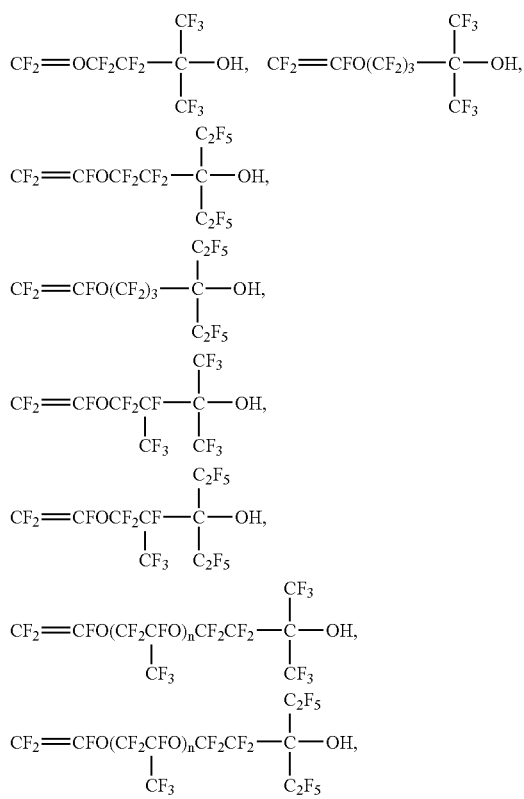

(n is an integer of from 1 to 30)

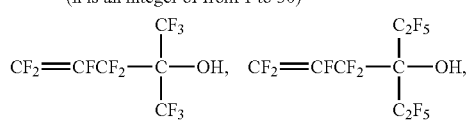

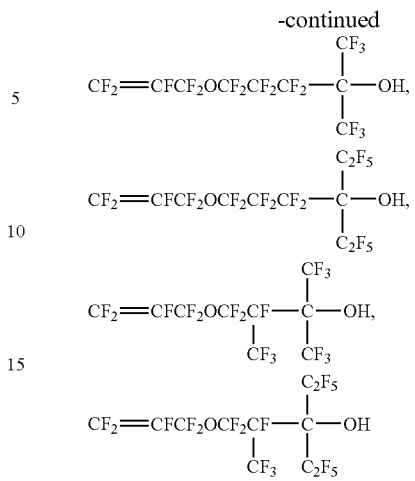

and the like.

To obtain the fluorine-containing ethylenic monomer having hydroxyl of the present invention, various preparation processes can be employed, and any of the processes may be employed.

Particularly the following preparation process is preferred.

A fluorine-containing ethylenic monomer having carboxyester group or acid halide group which is represented by the formula (9):

$$CX^1X^2=CX^3-(Rf^3)_a-(C=O)Z^1 \tag{9}$$

wherein $Z^1$ is $OR^1$ in which $R^1$ is a hydrocarbon group having 1 to 10 carbon atoms, or halogen atom; $X^1$, $X^2$, $X^3$, $Rf^3$ and a are as defined in the formula (1), is used as a starting material. With the monomer of the formula (9) are reacted an organometallic compound represented by the formula (10):

$$Rf^1M^1X^4 \text{ or } Rf^1M^2 \tag{10}$$

wherein $M^1$ is a metal atom selected from the group consisting of Mg, Ca, Zn, Cd, Hg, Co, Mn and Cu; $M^2$ is an alkali metal atom; $X^4$ is halogen atom; $Rf^1$ is as defined in the formula (1), and/or an organometallic compound represented by the formula (11):

$$Rf^2M^1X^4 \text{ or } Rf^2M^2X^4 \tag{11}$$

wherein $M^1$, $M^2$ and $X^4$ are as defined in the formula (10); $Rf^2$ is as defined in the formula (1). With the monomer of the formula (9) is reacted either of the organometallic compounds (10) and (11) in an amount of two equivalents or more to the monomer or is reacted the both of the organometallic compounds (10) and (11) in an amount of one equivalent or more, respectively (two equivalents or more in total) to the monomer, and then thereon is acted a protonic acid. Thus the monomer having hydroxyl can be prepared.

In the formula (9), preferred $Z^1$ are $OCH_3$, $OC_2H_5$, $OC_3H_7$, $OC_4H_9$, F, Cl, Br, I and the like, and particularly preferred are $OCH_3$, $OC_2H_5$, F and Cl.

Example of the monomer of the formula (9) is one represented by:

$$CH_2=CFCF_2-(Rf^4)_a-(C=O)Z^1 \tag{9-1}$$

wherein $Z^1$ is as defined in the formula (9); $Rf^4$ and a are as defined in the formula (2), or

 (9)-2 wherein $Z^1$ is as defined in the formula (9); $Rf^5$ and a are as defined in the formula (3).

In the formulae (9), (9)-1 and (9)-2, a is 0 or 1. Namely, the monomers may have or may not have $Rf^3$, $Rf^4$ and $Rf^5$, respectively.

When a is 0 in the formula (9), the monomer is concretely one represented by:

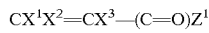

wherein $Z^1$ is as defined in the formula (9); $X^1$, $X^2$ and $X^3$ are as defined in the formula (4), and more concretely there are:

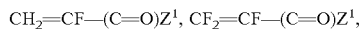

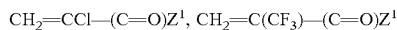

and the like.

When a is 1 in the formulae (9), (9)-1 and (9)-2, $Rf^3$ and $Rf^5$ are selected from a fluorine-containing alkylene group having 1 to 40 carbon atoms and a fluorine-containing alkylene group having 1 to 100 carbon atoms and ether bond, and $Rf^4$ is selected from a fluorine-containing alkylene group having 1 to 39 carbon atoms and a fluorine-containing alkylene group having 1 to 99 carbon atoms and ether bond. Preferable examples thereof are the same as described in the formulae (1) to (3).

In the present invention, when a is 1, examples of the particularly preferable fluorine-containing ethylenic monomer of the formula (9) are:

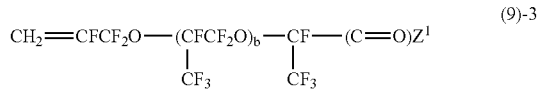

wherein $Z^1$ is as defined in the formula (9); b is an integer of from 1 to 13, and

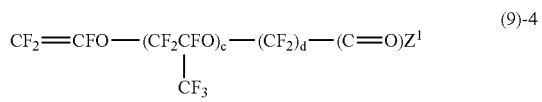

wherein $Z^1$ is as defined in the formula (9); c is an integer of from 1 to 13; d is an integer of from 1 to 5.

In the organometallic compounds of the formulae (10) and (11) to be reacted with the fluorine-containing ethylenic monomer of the formula (9), $M^1$ is a metal atom selected from the group consisting of Mg, Ca, Zn, Cd, Hg, Co, Mn and Cu, and $M^2$ is selected from alkali metal atoms. Particularly preferred are Mg, Zn and Li from the viewpoint of good reactivity with carboxyester group and acid halide group in the monomer of the formula (9) and good stability of the compounds of the formulae (10) and (11). $X^4$ is selected from halogen atoms, and I, Br and Cl are preferred and I and Br are more preferred.

Examples of the preferred organometallic compounds of the formulae (10) and (11) are $Rf^1MgI$, $Rf^1MgBr$, $Rf^1ZnI$, $Rf^1ZnBr$, $Rf^2MgI$, $Rf^2MgBr$, $Rf^2ZnI$, $Rf^2ZnBr$ and the like.

More concrete examples of the preferable compounds are $CF_3MgI$, $C_2F_5MgI$, $C_4F_9MgI$, $CF_3MgBr$, $C_2F_5MgBr$, $C_4F_9MgBr$, $CF_3ZnI$, $C_2F_5ZnI$, $C_4F_9ZnI$, $CF_3Li$, $C_2F_5Li$, $C_4F_9Li$ and the like.

A process for synthesizing the compound of the formula (10) or (11) varies depending on kind of the intended compound of the formula (10) or (11) and is optionally selected. For example, the compound of the formula (10) or (11) can be prepared by reacting perfluoroalkyl halide represented by the formula (12):

 (12)

wherein $X^6$ is halogen atom; $Rf^1$ and $Rf^2$ are as defined in the formulae (10) and (11), directly with a metal corresponding to the metal atom $M^1$ or $M^2$ contained in the organometallic compound of the formula (10) or (11), for example, magnesium, zinc, lithium or the like. In that case, it is more preferable to add a small amount of iodine, bromine, methyl iodide, ethyl iodide, ethyl bromide or the like as a catalyst from the point that a reaction can be initiated smoothly.

The organometallic compound can also be prepared by reacting the perfluoroalkyl halide of the formula (12) with an organometallic compound which is previously produced by known process and is represented by the formula (13):

 (13)

wherein $R^2$ is a hydrocarbon group having 1 to 10 carbon atoms; $X^5$ is halogen atom; $M^1$ and $M^2$ are the same as $M^1$ and $M^2$ of the formulae (10) and (11). Particularly when the compound of the formula (10) or (11) in which $M^1$ is magnesium or $M^2$ is lithium is intended to obtain, preferred is a process for reacting the organometallic compound of the formula (13) ($M^1$ is magnesium or $M^2$ is lithium) with the perfluoroalkyl halide of the formula (12).

Examples of preferred organometallic compound of the formula (13) are $CH_3MgI$, $CH_3MgBr$, $C_2H_5MgI$, $C_2H_5MgBr$, $C_4H_9MgI$, $C_4H_9MgBr$, $C_6H_5MgI$, $C_6H_5MgBr$, $C_6H_5$—$CH_2MgI$, $C_6H_5$—$CH_2MgBr$, $CH_3Li$, $C_2H_5Li$, $C_4H_9Li$, $C_6H_5Li$, $C_6H_5$—$CH_2Li$ and the like.

For synthesizing the compound of the formula (10) or (11), it is generally preferable to use, as a reaction solvent, an aprotic polar solvent or a cyclic or acyclic ether solvent.

Examples of the preferred solvent are tetrahydrofuran, dioxane, monoglyme, diglyme, triglyme, tetraglyme, methyl-t-butyl ether, acetonitrile, benzonitrile, sulfolane, N,N-dimethylformamide, N,N-dimethylacetoamide and the like.

A reaction temperature is optionally selected depending on kind of the intended compound of the formula (10) or (11) and is preferably from −80° C. to +120° C., more preferably not more than +10° C., particularly as low as not more than −10° C.

The fluorine-containing ethylenic monomers having hydroxyl of the formulae (1) to (6) of the present invention can be prepared by reacting the compound of the formula (10) or (11) obtained by the above-mentioned process with the fluorine-containing ethylenic monomer of the formula (9) having carboxyester group or acid halide group and corresponding to the intended structure and then acting a protonic acid thereon.

In the reaction of the monomer of the formula (9) with the compound of the formula (10) or (11), it is generally preferable to use, as a reaction solvent, an aprotic polar solvent or a cyclic or acyclic ether solvent.

Examples of the preferred solvent are tetrahydrofuran, dioxane, monoglyme, diglyme, triglyme, tetraglyme, methyl-t-butyl ether, acetonitrile, benzonitrile, sulfolane, N,N-dimethylformamide, N,N-dimethylacetoamide and the like.

A reaction temperature varies depending on kinds of the monomer of the formula (9), the compound of the formula (10) or (11) and the intended fluorine-containing ethylenic monomer having hydroxyl and is optionally selected. The reaction temperature is preferably from −80° C. to +120° C., more preferably not more than +10° C., particularly as low as not more than −10° C.

A reaction time varies depending on kinds of the monomer of the formula (9) and the compound of the formula (10) or (11) and is optionally selected. The reaction time is preferably from 10 minutes to 100 hours, more preferably from 30 minutes to 10 hours.

Examples of preferred protonic acid to be used after the reaction are hydrochloric acid, sulfuric acid, nitric acid and the like. It is generally preferable to use those acids in the form of an aqueous solution. A concentration of the protonic acid is not limited.

Also when reacting with the protonic acid, an alcohol such as methanol, ethanol or isopropyl alcohol may be used as a reaction solvent.

A reaction temperature when reacting with the protonic acid is from −20° C. to +100° C., particularly preferably from 0° C. to 40° C., and a reaction time is from one minute to 10 hours, particularly preferably from 10 minutes to five hours.

In the reaction of the fluorine-containing ethylenic monomer of the formula (9) having carboxyester group or acid halide group with the compound of the formula (10) or (11), first a ketone compound corresponding to the intended monomer and represented by the formula (14):

(14)

wherein $X^1$, $X^2$, $X^3$, $Rf^1$, $Rf^3$ and a are as defined in the formula (1), is produced, and further the compound of the formula (10) or (11) acts on the ketone compound (14) and then after acid hydrolysis, the intended fluorine-containing ethylenic monomer (1) having hydroxyl can be obtained. The ketone compound of the formula (14) may be once isolated and then reacted with the compound of the formula (10) or (11), or the ketone compound may be continuously reacted with the compound of the formula (10) or (11) without being isolated. When synthesizing the intended monomer having hydroxyl by using $Rf^1$ and $Rf^2$ having the same structure, it is particularly efficient and preferable to react the compounds of the formulae (10) and (11) in an amount of two or more moles to 1 mole of the fluorine-containing ethylenic monomer of the formula (9) having carboxyester group or acid halide group without isolating the ketone compound of the formula (14).

On the contrary, when synthesizing the intended monomer having hydroxyl by using $Rf^1$ and $Rf^2$ having the different structures, it is preferable to react one of the compounds of the formulae (10) and (11) in an equimolar amount or a little excessive amount (for example, from 1 to 1.2 mole) to 1 mole of the monomer of the formula (9) and then react another one of the compounds of the formula (10) and (11) having a different structure in an equimolar amount or a little excessive amount (for example, from 1 to 1.2 mole) to 1 mole of the monomer of the formula (9). In this case, too, the ketone compound (14) generated in the midst of the reaction may be isolated or may be continuously reacted with the compound of the formula (10) and (11) by the above-mentioned procedures without isolation.

The second of the present invention relates to the novel fluorine-containing polymer prepared by (co)polymerizing the fluorine-containing ethylenic monomer of the present invention having hydroxyl.

The fluorine-containing polymer of the present invention is a fluorine-containing polymer having a number average molecular weight of from 500 to 1,000,000 which is represented by the formula (7):

-(M)-(A)- (7)

wherein the structural unit M is a structural unit derived from the fluorine-containing ethylenic monomer having hydroxyl of the present invention which is selected from any of the formulae (1) to (6), the structural unit A is a structural unit derived from monomer copolymerizable with the structural unit M, and the structural unit M and the structural unit A are contained in amounts of from 0.1 to 100% by mole and from 0 to 99.9% by mole, respectively.

Namely, the fluorine-containing polymer of the present invention is a homopolymer of the novel fluorine-containing ethylenic monomer of a specific structure having hydroxyl at an end of its side chain or a copolymer comprising such a fluorine-containing ethylenic monomer as an essential component.

In the fluorine-containing polymer of the present invention, the structural unit M of the fluorine-containing ethylenic monomer having hydroxyl is selected from the fluorine-containing ethylenic monomers of the above-mentioned formulae (1) to (6) and also preferable examples thereof are the same as the above-mentioned monomers.

In the fluorine-containing polymer of the present invention, the structural unit A is an optional component. The structural unit A is not limited particularly as far as it is a monomer copolymerizable with the structural unit M. The structural unit A may be optionally selected depending on intended applications and required characteristics of the fluorine-containing polymer.

Examples of the structural unit A are, for instance, as follows.

① Structural Units Derived from Fluorine-containing Ethylenic Monomers Having Functional Group (Except the Fluorine-containing Ethylenic Monomer of the Present Invention Having Hydroxyl at an End Thereof)

These structural units are preferred from the point that adhesion to a substrate and solubility in a solvent, particularly a general-purpose solvent can be imparted to the fluorine-containing polymer while maintaining a low refractive index and a high transparency of the polymer, and are also preferred from the point that other functions such as crosslinkability can be imparted. Preferred structural unit of the fluorine-containing ethylenic monomer having functional group is a structural unit represented by the formula (15):

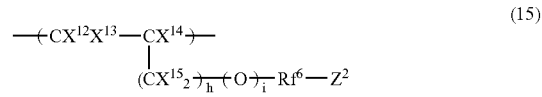

(15)

wherein $X^{12}$, $X^{13}$ and $X^{14}$ are the same or different and each is H or F; $X^{15}$ is H, F or $CF_3$; h is 0, 1 or 2; i is 0 or 1; $Rf^6$ is a fluorine-containing alkylene group having 1 to 40 carbon atoms or a fluorine-containing alkylene group having 2 to 100 carbon atoms and ether bond; $Z^2$ is OH, $CH_2OH$, COOH, carboxylic acid derivative, $SO_3H$, sulfonic acid derivative, epoxy or cyano, and particularly preferred is a structural unit derived from a monomer represented by:

$$CH_2=CFCF_2ORf^6-Z^2$$

wherein $Rf^6$ and $Z^2$ are as defined in the formula (15).

More concretely there are preferably structural units derived from fluorine-containing ethylenic monomers such as:

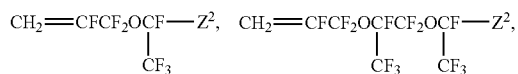
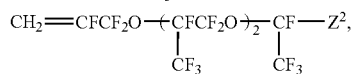
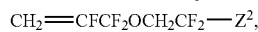
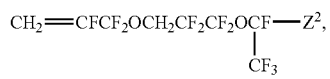

Also there is a preferred structural unit derived from a monomer represented by:

$$CF_2=CFORf^6-Z^2$$

wherein $Rf^6$ and $Z^2$ are as defined in the formula (15). More concretely there are structural units derived from monomers such as:

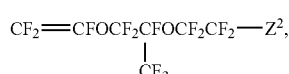
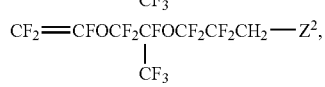

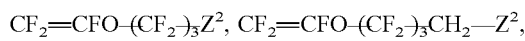

$CF_2=CFOCF_2CF_2OCF_2-Z^2$, $CF_2=CFOCF_2CF_2OCF_2CH_2-Z^2$, $CF_2=CFOCF_2CF_2CH_2OCF_2CF_2-Z^2$ and $CF_2=CFOCF_2CF_2CH_2OCF_2CF_2CH_2-Z^2$.

Examples of the other fluorine-containing ethylenic monomer having functional group are:

$CF_2=CFCF_2-O-Rf^6-Z^2$, $CF_2=CF-Rf^6-Z^2$, $CH_2=CH-Rf^6-Z^2$, $CH_2=CHO-Rf^6-Z^2$, and the like, wherein $Rf^6$ is as defined in the formula (15).

More concretely there are:

$CF_2=CFCF_2OCF_2CF_2CF_2-Z^2$.

$CF_2=CFCF_2OCF_2CF_2CF_2CH_2-Z^2$.

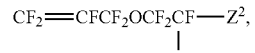

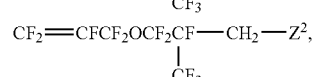

$CF_2=CFCF_2-Z^2$, $CF_2=CFCF_2CH_2-Z^2$, $CH_2=CHCF_2OF_2CH_2CH_2-Z^2$,
$CH_2=CHCF_2CF_2-Z^2$, $CH_2=CHCF_2CF_2CH_2-Z^2$,
$CH_2=CHCF_2CF_2CF_2CF_2-Z^2$, $CH_2=CHCF_2CF_2CF_2CH_2-Z^2$, $CH_2=CHO-$
$CH_2CF_2CF_2-Z^2$, $CH_2=CHOCH_2CF_2CF_2CH_2-Z^2$ and the like.

② Structural Units Derived from Fluorine-containing Ethylenic Monomers Having no Functional Group.

These structural units are preferred from the point that a low refractive index of the fluorine-containing polymer can be maintained and the refractive index thereof can be further decreased and also from the point that transparency can be increased. Further these structural units are preferred from the point that by selecting the monomer, mechanical properties and glass transition temperature of the polymer can be adjusted, and particularly the glass transition temperature can be increased by copolymerization with the structural unit M.

Examples of the preferred structural unit of the fluorine-containing ethylenic monomer are those represented by the formula (16):

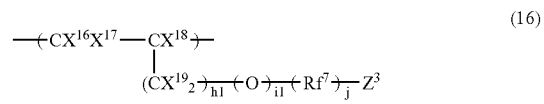
(16)

wherein $X^{16}$, $X^{17}$ and $X^{18}$ are the same or different and each is H or F; $X^{19}$ is H, F or $CF_3$; h1, i1 and j are 0 or 1; $Z^3$ is H, F or Cl; $Rf^7$ is a fluorine-containing alkylene group having 1 to 20 carbon atoms or a fluorine-containing alkylene group having 2 to 100 carbon atoms and ether bond.

Among them, preferred as the structural unit A are structural units of fluorine-containing ethylenic monomers having no hydroxyl which is represented by the formula (8):

$$CX^4X^5=CX^6X^7 \quad (8)$$

wherein $X^4$ and $X^5$ are the same or different and each is H or F; $X^6$ is H, F or $CF_3$; $X^7$ is H, F, Cl or $CF_3$; at least one of $X^4$, $X^5$, $X^6$ and $X^7$ is F or $CF_3$, from the viewpoint of particularly good copolymerizability with the fluorine-containing ethylenic monomer having hydroxyl of the present invention.

Examples thereof are monomers such as:

$CF_2=CF_2$, $CF_2=CH_2$, $CF_2=CFCl$, $CF_2=CFCF_3$,

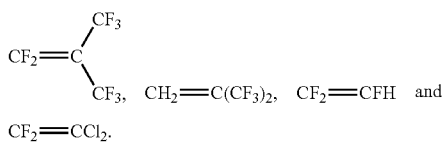

Also there are preferably structural units derived from monomers such as:

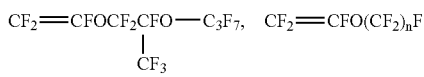

(n: from 1 to 5), $CH_2=CF\text{-}(CF_2)_n\text{-}Z^3$ ($Z^3$ is as defined in the formula (16), n: from 1 to 10) and $CH_2=CHOCH_2\text{-}(CF_2)_n\text{-}Z^3$ ($Z^3$ is as defined in the formula (16), n: from 1 to 10)

③ Fluorine-containing Aliphatic Ring Structural Units

Introduction of these structural units is preferred since transparency can be increased and a lower refractive index can be obtained and further since a curable fluorine-containing polymer having a high glass transition temperature can be obtained and a high hardness can be expected.

Examples of the preferred fluorine-containing aliphatic ring structural unit are those represented by the formula (17):

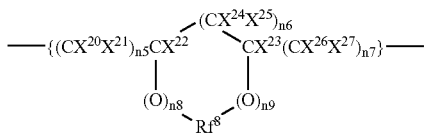

(17)

wherein $X^{20}$, $X^{21}$, $X^{24}$ $X^{25}$, $X^{26}$ and $X^{27}$ are the same or different and each is H or F; $X^{22}$ and $X^{23}$ are the same or different and each is H, F, Cl or $CF_3$; $Rf^8$ is a fluorine-containing alkylene group having 1 to 10 carbon atoms or a fluorine-containing alkylene group having 2 to 10 carbon atoms and ether bond; n6 is 0 or an integer of from 1 to 3; n5, n7, n8 and n9 are the same or different and each is 0 or 1.

For example, there are structural units represented by:

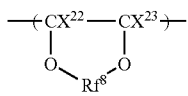

wherein $Rf^8$, $X^{22}$ and $X^{23}$ are as defined in the formula (17).

Concretely there are:

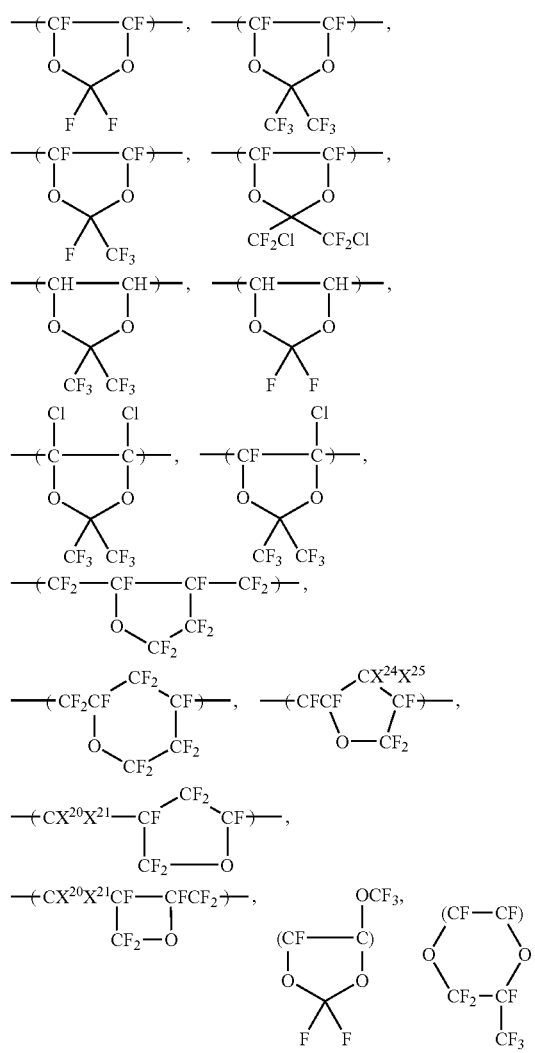

and the like wherein $X^{20}$, $X^{21}$, $X^{24}$ and $X^{25}$ are as defined in the formula (17).

Examples of other monomers giving the fluorine-containing aliphatic ring structural unit are, for instance,

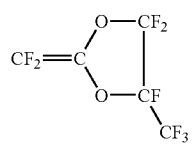

and the like.

④ Structural Units Derived from Ethylenic Monomers Having No Fluorine

The structural units derived from ethylenic monomers having no fluorine may be introduced to the polymer within a range where the introduction does not have an adverse effect on a refractive index (within a range where the refractive index does not increase).

The introduction of these structural units is preferred since solubility in a general-purpose solvent is enhanced and compatibility with additives, for example, a photoacid generator and a curing agent to be added as case demands can be improved.

Examples of the non-fluorine-containing ethylenic monomer are as follows.

α-Olefins:

Ethylene, propylene, butene, vinyl chloride, vinylidene chloride and the like.

Vinyl Ether or Vinyl Ester Monomers:

$CH_2$=CHOR, $CH_2$=CHOCOR (R: hydrocarbon group having 1 to 20 carbon atoms) and the like.

Allyl Monomers:

$CH_2$=CHCH$_2$Cl, $CH_2$=CHCH$_2$OH, $CH_2$=CHCH$_2$COOH, $CH_2$=CHCH$_2$Br and the like.

Allyl Ether Monomers:

$CH_2$=CHCH$_2$OR (R: hydrocarbon group having 1 to 20 carbon atoms), $CH_2$=CHCH$_2$OCH$_2$CH$_2$COOH, $CH_2$=CHCH$_2$OCH$_2$CHCH$_2$ (with epoxide), $CH_2$=CHCH$_2$OCH$_2$CHCH$_2$ (with OH, OH)

and the like.

Acrylic or Methacrylic Monomers:

Acrylic acid, methacrylic acid, acrylic acid esters, methacrylic acid esters, maleic anhydride, maleic acid, maleic acid esters and the like.

⑤ Structural Units Derived from Alicyclic Monomers

A structural unit of an alicyclic monomer may be introduced as a component copolymerizable with the structural unit M, more preferably as the third component in addition to the structural unit M and the structural unit of the above-mentioned fluorine-containing ethylenic monomer or non-fluorine-containing ethylenic monomer (the above-mentioned ③ or ④ ), which is preferred since a high glass transition temperature and a high hardness can be obtained.

Examples of the alicyclic monomer are norbornene derivatives represented by:

wherein m is from 0 to 3; A, B, C and D are the same or different and each is H, F, Cl, COOH, CH$_2$OH, a perfluoroalkyl group having 1 to 5 carbon atoms or the like, alicyclic monomers such as:

and derivatives thereof in which a substituent is introduced.

In the fluorine-containing polymer of the present invention, various combinations and proportions of the structural units M and A can be selected from the above-mentioned examples depending on intended applications, physical properties (particularly glass transition temperature, hardness, etc.), functions (transparency and refractive index) and the like.

The fluorine-containing polymer of the present invention contains the structural unit M as an essential component and has functions due to the structural unit M itself such as maintaining a low refractive index and imparting transparency to the polymer, and functions due to hydroxyl such as imparting solubility in a solvent, solubility in an aqueous alkaline solution, adhesion to a substrate and crosslinkability. Therefore even if the fluorine-containing polymer of the present invention contains a larger amount of the structural unit M or in the extreme case, even if the polymer consists of the structural unit M (100% by mole), transparency and the refractive index can be maintained.

Also in the case of the copolymer of the present invention comprising the structural unit M and the structural unit A of the copolymerizable monomer, when the structural unit A is selected from the above-mentioned examples, the fluorine-containing polymer having higher hardness (high glass transition temperature), a low refractive index and a high transparency can be obtained.

In the copolymer comprising the structural unit M and the structural unit A, the proportion of the structural unit M may be not less than 0.1% by mole based on the whole monomers constituting the fluorine-containing polymer. The proportion is not less than 2.0% by mole, preferably not less than 5% by mole, more preferably not less than 10% by mole in order to obtain the cured article having a high hardness, excellent abrasion resistance and scratch resistance and good chemical resistance and solvent resistance by curing (crosslinking).

Particularly for the antireflection film application which requires formation of a cured coating film having excellent scratch resistance and damage resistance, it is preferable that the structural unit M is contained in an amount of not less than 10% by mole, preferably not less than 20% by mole, more preferably not less than 50% by mole.

Further in order to impart solubility in an aqueous alkaline solution and water solubility to the fluorine-containing polymer, it is preferable that the structural unit M is contained in an amount of not less than 10% by mole, preferably not less than 20% by mole, more preferably not less than 30% by mole.

The fluorine-containing polymer of the present invention is preferable particularly for the antireflection film and resist applications since neither a refractive index is increased nor transparency is lowered even if the proportion of the structural unit M is increased.

Also in the case of the above-mentioned applications requiring transparency, preferred combinations and proportions of the structural units M and A are those which can make the fluorine-containing polymer non-crystalline.

The molecular weight of the fluorine-containing polymer of the present invention can be selected, for example, in a range of from 500 to 1,000,000 in number average molecular weight. Preferred molecular weight is from 1,000 to 500,000, particularly from 2,000 to 200,000.

When the molecular weight is too low, mechanical properties are apt to be insufficient, and particularly the cured article and cured coating film become fragile and are apt to be insufficient in strength. If the molecular weight is too high, solubility in a solvent is lowered, and film forming property and leveling property tend to be lowered particularly at forming a thin coating film. For coating applications, most preferable number average molecular weight is selected in a range of from 5,000 to 100,000.

In the fluorine-containing polymer of the present invention, though various refractive indices can be selected depending on kind and content of the structural unit M and kind of the structural unit A to be used as case demands, the refractive index of the fluorine-containing polymer itself (before curing) is preferably not more than 1.45, more preferably not more than 1.40, particularly preferably not more than 1.38 when curability is imparted to the polymer. The refractive index changes depending on kinds of a substrate and undercoating, but since the curing (crosslinking) can be done while maintaining a low refractive index, the polymer can be a preferable base polymer for an antireflection film.

The refractive index is determined by casting a reaction product in a Petri dish to form a film and measuring a refractive index ($n^D$) of the film at 589 nm by using Abbe's refractometer 2T available from Kabushiki Kaisha Atago.

With respect to transparency, it is preferable that the polymer is transparent in case of vacuum ultraviolet light having a wavelength of not more than 200 nm. For example, an absorption coefficient at 157 nm is not more than 4.0 $\mu m^{-1}$, preferably not more than 3.0 $\mu m^{-1}$, particularly preferably not more than 2.0 $\mu m^{-1}$. Such a polymer is preferable as a base polymer for a $F_2$ resist.

Also it is preferable that the fluorine-containing polymer is soluble in general-purpose solvents, for example in at least one of ketone solvents, acetic acid ester solvents, alcohol solvents, aromatic solvents, is glycol ether solvents or glycol ester solvents or in solvent mixtures containing at least one of the above-mentioned general-purpose solvents.

"Being soluble in the general-purpose solvents" is so defined that the polymer is soluble uniformly in the solvent in an amount of not less than 1% by weight. Good solubility means that the polymer is uniformly dissolved in an amount of not less than 10% by weight.

The fluorine-containing polymer of the present invention can be obtained by (co)polymerizing, through known method, the fluorine-containing ethylenic monomer having hydroxyl which corresponds to the structural unit M with the monomer of the structural unit A when used as a copolymerizable component. For the polymerization, radical polymerization method, anion polymerization method, cation polymerization method and the like can be employed. Among them, the radical polymerization method is preferably used from the point that each monomer exemplified to obtain the fluorine-containing polymer having hydroxyl of the present invention has good radial polymerizability, control of composition and molecular weight is easy and production in an industrial scale is easy.

In order to initiate the radical polymerization, means for initiation is not limited particularly as far as the polymerization proceeds radically. The polymerization is initiated, for example, with an organic or inorganic radical polymerization initiator, heat, light, ionizing radiation or the like. The polymerization can be carried out by solution polymerization, bulk polymerization, suspension polymerization, emulsion polymerization or the like. The molecular weight is controlled by the contents of monomers to be used for the polymerization, the content of polymerization initiator, the content of chain transfer agent, temperature, etc. The components of the copolymer can be controlled by the starting monomer components.

The fluorine-containing ethylenic monomer having a fluoroalkyl carbonyl group which is represented by the formula (14) is a fluoroalkyl ketone which has a carbon-carbon double bond having good radical polymerizability and a carbonyl group at another end thereof in which a fluorine-containing alkyl group is bonded to carbon of the carbonyl group. This monomer is a novel compound which has not been disclosed in any literatures. The fluorine-containing ethylenic monomer having a fluoroalkyl carbonyl group can be subjected to polymerization solely and can be copolymerized with other monomers, particularly a fluorine-containing ethylenic monomer having no fluoroalkyl carbonyl group. Therefore the fluorine-containing polymer obtained by the (co)polymerization is also a novel compound.

The fluoroalkyl carbonyl group being present in the novel fluorine-containing ethylenic monomer and polymer of the present invention is high in acid reactivity as compared with conventional carbonyl groups, and easily produces hemi-acetal, for example, by acid hydrolysis. Since hemi-acetal is unstable, it has been difficult to make hemi-acetal present stably in the monomer or polymer backbone. However according to the present invention, the hemi-acetal group can be introduced in a stable form to the fluorine-containing ethylenic monomer and fluorine-containing polymer and therefore various functions can be imparted to the fluorine-containing polymer.

Further it was found that the fluorine-containing polymer obtained by (co)polymerizing the novel fluorine-containing ethylenic monomer has a high transparency (particularly transparency in vacuum ultraviolet region), a low refractive index and further a high affinity for or solubility in an aqueous medium and an aqueous alkaline medium.

Namely, the third of the present invention relates to the novel fluorine-containing ethylenic monomer having fluoroalkyl carbonyl group.

The fluorine-containing ethylenic monomer having fluoroalkyl carbonyl group of the present invention is a fluorine-containing monomer represented by the formula (14):

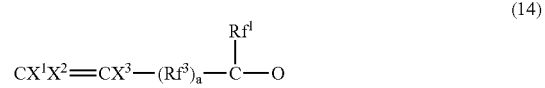

wherein $X^1$ and $X^2$ are the same or different and each is H or F; $X^3$ is H, F, Cl or $CF_3$; $Rf^1$ a perfluoroalkyl group having 1 to 20 carbon atoms; $Rf^3$ is a fluorine-containing alkylene group having 1 to 40 carbon atoms or a fluorine-containing alkylene group having ether bond which has 1 to 100 carbon atoms and the sum of carbon atom and oxygen atom of two or more; a is 0 or 1.

Particularly preferred is a fluorine-containing ethylenic monomer represented by the formula (21):

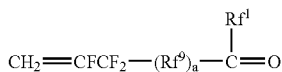

(21)

wherein $Rf^1$ is as defined in the formula (14); $Rf^9$ is a fluorine-containing alkylene group having 1 to 39 carbon atoms or a fluorine-containing alkylene group having 1 to 99 carbon atoms and ether bond; a is 0 or 1, from the viewpoint of good homopolymerizability and good copolymerizability with fluorine-containing ethylenic monomer having no fluoroalkyl carbonyl group such as tetrafluoroethylene and vinylidene fluoride.

Also preferred is a fluorine-containing ethylenic monomer represented by the formula (22):

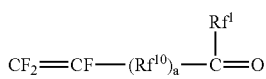

(22)

wherein $Rf^1$ is as defined in the formula (14); $Rf^{10}$ is a fluorine-containing alkylene group having 1 to 40 carbon atoms or a fluorine-containing alkylene group having 1 to 100 carbon atoms and ether bond; a is 0 or 1, from the viewpoint of good copolymerizability with the above-mentioned fluorine-containing ethylenic monomer having no carbonyl group such as tetrafluoroethylene and vinylidene fluoride.

In the formulae (14), (21) and (22), a is 0 or 1. This indicates that $Rf^3$, $Rf^9$ and $Rf^{10}$ may be contained or may not be contained in the respective monomers.

When a is 0, the monomer is one represented by the formula (23):

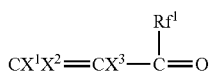

(23)

wherein $X^1$ and $X^2$ are the same or different and each is H or F; $X^3$ is H or F, Cl or $CF_3$; $Rf^1$ is as defined in the formula (14). More concretely there are:

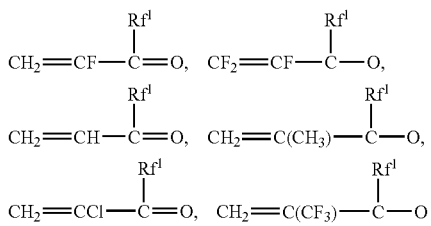

and the like, wherein $Rf^1$ is as defined in the formula (14).

In the formulae (14), (21) and (22), when a is 1, $Rf^3$ and $Rf^{10}$ are selected from a fluorine-containing alkylene group having 1 to 40 carbon atoms and a fluorine-containing alkylene group having 1 to 100 carbon atoms and ether bond and $Rf^9$ is selected from a fluorine-containing alkylene group having 1 to 39 carbon atoms and a fluorine-containing alkylene group having 1 to 99 carbon atoms and ether bond.

Examples of the preferred fluorine-containing alkylene groups $Rf^3$, $Rf^9$ and $Rf^{10}$ are:

—$(CF_2)_{n1}$— (n1 is an integer of 1 or more),

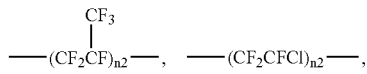

—$(CH_2CF_2)_{n2}$—, —$(CF_2CH_2)_{n2}$—, (n2 is an integer of 1 or more)

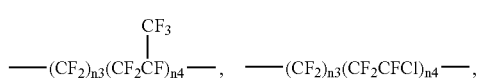

—$(CF_2)_{n3}(CH_2)_{n4}$—, (n3 and n4 are integers of 1 or more) and the like.

When $Rf^3$, $Rf^9$ and $Rf^{10}$ are fluorine-containing alkylene groups having ether bond, examples thereof are:

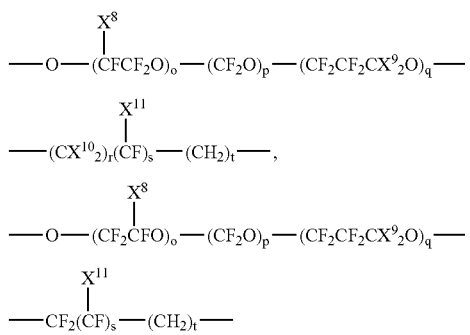

and the like, wherein $X^8$ and $X^{11}$ are the same or different and each is F or $CF_3$; $X^9$ and $X^{10}$ are the same or different and each is H or F; o+p+q is an integer of from 1 to 30; r is 0 or 1; s and t are 0 or 1.

Further in the present invention, examples of the preferred fluorine-containing ethylenic monomer having fluoroalkyl carbonyl group in the case of a=1 are those represented by the formula (24):

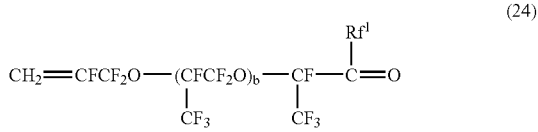

(24)

wherein $Rf^1$ is as defined in the formula (14); b is an integer of from 1 to 13, and the formula (25):

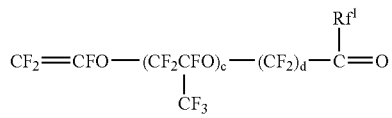

(25)

wherein $Rf^1$ is as defined in the formula (14); c is an integer of from 1 to 13; d is an integer of from 1 to 5.

In the fluorine-containing ethylenic monomers having fluoroalkyl carbonyl group of the formulae (14) to (25), $Rf^1$ is a perfluoroalkyl group and examples thereof are:

$F(CF_2)_{n1}$ (n1 is an integer of from 1 to 20),

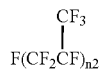

(n2 is an integer of from 1 to 6),

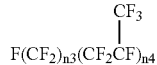

(n3 and n4 are integers which make the sum of carbon atoms of 20 or less)

and the like, and among them, preferred are $CF_3$, $C_2F_5$, $C_3F_7$, $C_4F_9$, $(CF_3)_2CF$ and the like.

More concrete examples of the fluorine-containing ethylenic monomer having fluoroalkyl carbonyl group of the present invention are:

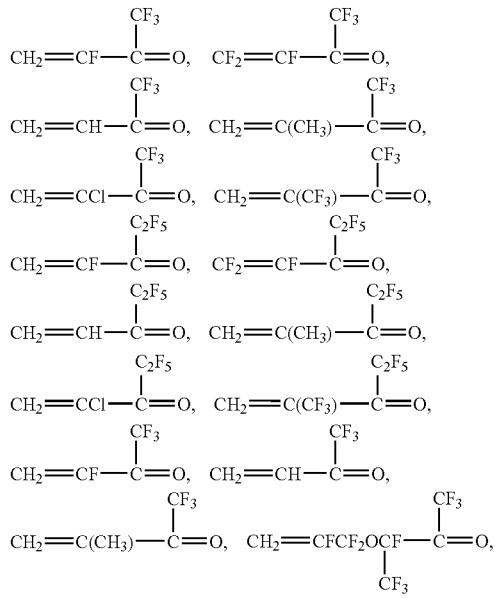

-continued

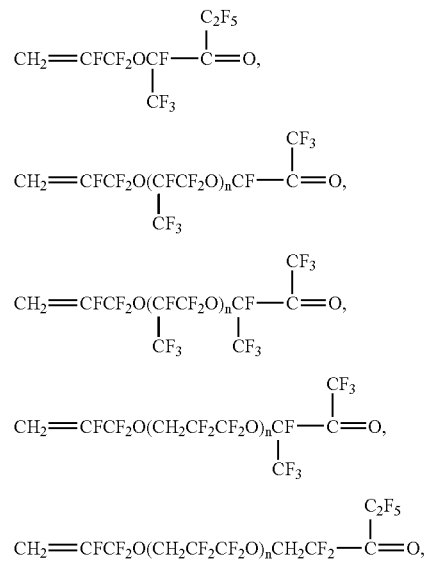

(n in above are all an integer of from 1 to 30)

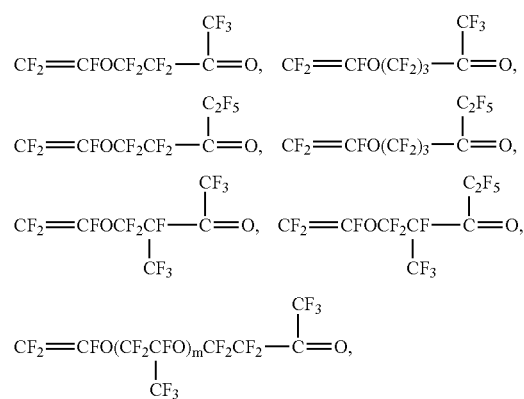

(m in above are all an integer of from 1 to 30)

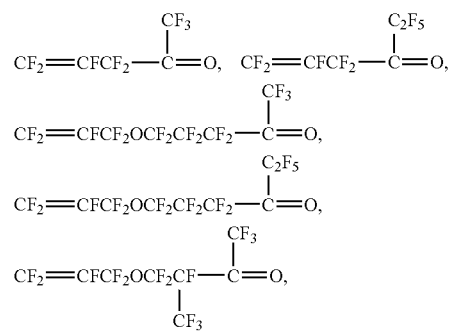

-continued

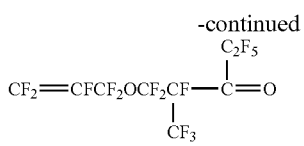

and the like.

For preparing the fluorine-containing ethylenic monomer having fluoroalkyl carbonyl group of the present invention, various preparation processes may be employed.

Among them, preferred is the following preparation process.

A fluorine-containing monomer having carboxyester group or acid halide group which is represented by the formula (26):

$$CX^1X^2=CX^3-(Rf^3)_a-(C=O)Z^1 \quad (26)$$

wherein $Z^1$ is $OR^1$ in which $R^1$ is a hydrocarbon group having 1 to 10 carbon atoms, or halogen atom; $X^1$, $X^2$, $X^3$, $Rf^3$ and a are as defined in the formula (14), is used as a starting material. With the monomer of the formula (26) is reacted an organometallic compound represented by the formula (27):

$$Rf^1M^1X^4 \text{ or } Rf^1M^2 \quad (27)$$

wherein $M^1$ is a metal atom selected from the group consisting of Mg, Ca, Zn, Cd, Hg, Co, Mn and Cu; $M^2$ is an alkali metal atom; $X^4$ is halogen atom; $Rf^1$ is as defined in the formula (14), in an amount of from equimolar amount to a little excessive amount (for example, 1 to 1.2 times in the number of moles) to the monomer of the formula (26). Thus the monomer having fluoroalkyl carbonyl group can be prepared.

In the formula (26), examples of the preferred $Z^1$ are $OCH_3$, $OC_2H_5$, $OC_3H_7$, $OC_4H_9$, F, Cl, Br, I and the like, and among them, particularly preferred are $OCH_3$, $OC_2H_5$, F and Cl.

Example of the monomer of the formula (26) is:

$$CH_2=CFCF_2-(Rf^9)_a-(C=O)Z^1 \quad (26)\text{-}1$$

wherein $Z^1$ is as defined in the formula (26); $Rf^9$ and a are as defined in the formula (21) or:

$$CF_2=CF-(Rf^{10})_a-(C=O)Z^1 \quad (26)\text{-}2$$

wherein $Z^1$ is as defined in the formula (26); $Rf^{10}$ and a are as defined in the formula (22).

In the formulae (26), (26)-1 and (26)-2, a is 0 or 1. Namely, this indicates that $Rf^3$, $Rf^9$ and $Rf^{10}$ may be contained or may not be contained in the respective monomers.

In the formula (26), when a is 0, the monomer is one represented by:

$$CX^1X^2=CX^3-(C=O)Z^1$$

wherein $Z^1$ is as defined in the formula (26); $X^1$, $X^2$ and $X^3$ are as defined in the formula (23). More concretely there are:

$$CH_2=CF-(C=O)Z^1, CF_2=CF-(C=O)Z^1,$$

$$CH_2=CH-(C=O)Z^1, CH_2=C(CH_3)-(C=O)Z^1,$$

$$CH_2=CCl-(C=O)Z^1, CH_2=C(CF_3)-(C=O)Z^1$$

and the like.

In the formulae (26), (26)-1 and (26)-2, when a is 1, $Rf^3$ and $Rf^{10}$ are selected from a fluorine-containing alkylene group having 1 to 40 carbon atoms and a fluorine-containing alkylene group having 1 to 100 carbon atoms and ether bond, and $Rf^9$ is selected from a fluorine-containing alkylene group having 1 to 39 carbon atoms or a fluorine-containing alkylene group having 1 to 99 carbon atoms and ether bond. Examples thereof are preferably the same as in the above-mentioned formulae (14) to (22).

Examples of particularly preferred fluorine-containing ethylenic monomer of the formula (26) when a is 1 are:

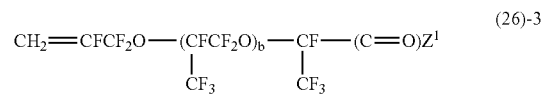

wherein $Z^1$ is as defined in the formula (26); b is an integer of from 1 to 13, and:

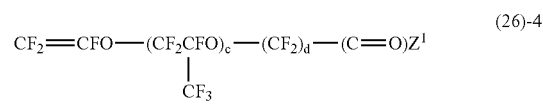

wherein $Z^1$ is as defined in the formula (26); c is an integer of from 1 to 13; d is an integer of from 1 to 5.

In the organometallic compound of the formula (27) which is reacted with those fluorine-containing ethylenic monomers of the formula (26), $M^1$ and $M^2$ are selected from the same metal atoms as above. Among them, Mg, Zn and Li are particularly preferred from the viewpoint of good reactivity with the carboxyester group and acid halide group in the monomer of the formula (26) and also good stability of the compound of the formula (27). $X^4$ is selected from halogen atoms, and preferred are I, Br and Cl and more preferred are I and Br.

Examples of the preferred organometallic compound of the formula (27) are $Rf^1MgI$, $Rf^1MgBr$, $Rf^1ZnI$, $Rf^1ZnBr$ and the like.

Further more concretely there are preferably $CF_3MgI$, $C_2F_5MgI$, $C_4F_9MgI$, $CF_3MgBr$, $C_2F_5MgBr$, $C_4F_9MgBr$, $CF_3ZnI$, $C_2F_5ZnI$, $C_4F_9ZnI$, $CF_3Li$, $C_2F_5Li$, $C_4F_9Li$ and the like.

A process for synthesizing the compound of the formula (27) varies depending on kind of the intended compound of the formula (27) and is optionally selected. For example, the compound can be obtained by reacting a perfluoroalkyl halide represented by the formula (28):

$$Rf^1X^6 \quad (28)$$

wherein $X^6$ is halogen atom; $Rf^1$ is as defined in the formula (27), directly with a metal corresponding to the metal atom $M^1$ or $M^2$ contained in the organometallic compound of the formula (27), for example, magnesium, zinc, lithium or the like. In this case, it is more preferable to add, as a catalyst, a small amount of iodine, bromine, methyl iodide, ethyl iodide, ethyl bromide or the like, from the point that the reaction can be initiated smoothly.

Also the compound of the formula (27) can be obtained by reacting the perfluoroalkyl halide of the formula (28) with an organometallic compound previously prepared by known process and represented by the formula (29):

$$R^2M^1X^5 \text{ or } R^2M^2 \qquad (29)$$

wherein $R^2$ is a hydrocarbon group having 1 to 10 carbon atoms; $X^5$ is halogen atom; $M^1$ and $M^2$ are the same as $M^1$ and $M^2$ of the formula (27), respectively. Particularly when aiming at the compound of the formula (27) in which $M^1$ is magnesium, it is preferable to react the organometallic compound ($M^1$ is magnesium) of the formula (29) with the perfluoroalkyl halide of the formula (28).

Examples of the preferred organometallic compound of the formula (29) are $CH_3MgI$, $CH_3MgBr$, $C_2H_5MgI$, $C_2H_5MgBr$, $C_4H_9MgI$, $C_4H_9MgBr$, $C_6H_5MgI$, $C_6H_5MgBr$, $C_6H_5$—$CH_2MgI$, $C_6H_5$—$CH_2MgBr$, $CH_3Li$, $C_2H_5Li$, $C_4H_9Li$, $C_6H_5Li$, $C_6H_5$—$CH_2Li$ and the like.

For synthesizing the compound of the formula (27), generally it is preferable to use an aprotic polar solvent or a cyclic or acyclic ether solvent as a reaction solvent.

Examples thereof are preferably tetrahydrofuran, dioxane, monoglyme, diglyme, triglyme, tetraglyme, methyl-t-butyl ether, acetonitrile, benzonitrile, sulfolane, N,N-dimethylformamide, N,N-dimethylacetoamide and the like.

A reaction temperature is optionally selected depending on kind of the intended compound of the formula (27) and is preferably from −80° C. to +120° C. It is preferable to react at low temperatures of not more than +10° C., particularly not more than −10° C.

The fluorine-containing ethylenic monomers having fluoroalkyl carbonyl group of the formulae (14) to (25) of the present invention can be obtained by reacting the fluorine-containing ethylenic monomer of the formula (26) having carboxyester group or acid halide group which corresponds to the intended structure, with the compound of the formula (27) obtained by the above-mentioned process.

For the reaction of the monomer of the formula (26) with the compound of the formula (27), generally it is preferable to use an aprotic polar solvent or a cyclic or acyclic ether solvent as a reaction solvent.

Examples thereof are preferably tetrahydrofuran, dioxane, monoglyme, diglyme, triglyme, tetraglyme, methyl-t-butyl ether, acetonitrile, benzonitrile, sulfolane, N,N-dimethylformamide, N,N-dimethylacetoamide and the like.

A reaction temperature varies depending on kinds of the monomer of the formula (26), the compound of the formula (27) and the intended fluorine-containing ethylenic monomer having fluoroalkyl carbonyl group and is optionally selected. The reaction temperature is preferably from −80° C. to +120° C. It is preferable to react at low temperatures of not more than +10° C., particularly not more than −10° C.

A reaction time varies depending on kinds of the monomer of the formula (26) and the compound of the formula (27) and is optionally selected. The reaction time is preferably from ten minutes to 100 hours, more preferably from 30 minutes to 10 hours.

The novel fluorine-containing polymer can be obtained by (co)polymerizing the novel fluorine-containing ethylenic monomer having fluoroalkyl carbonyl group of the present invention.

The fluorine-containing polymer of the present invention has a number average molecular weight of from 500 to 1,000,000 and is represented by the formula (30):

$$-(M1)-(A1)- \qquad (30)$$

wherein the structural unit M1 is a structural unit derived from the fluorine-containing ethylenic monomer having fluoroalkyl carbonyl group of the present invention which is selected from any of the monomers of the formulae (14) to (25), the structural unit A1 is a structural unit derived from monomer copolymerizable with the structural unit M1, and the structural unit M1 and the structural unit A1 are contained in amounts of from 0.1 to 100% by mole and from 0 to 99.9% by mole, respectively.

Namely, the fluorine-containing polymer of the present invention is a homopolymer of the novel fluorine-containing ethylenic monomer of a specific structure having fluoroalkyl carbonyl group at an end of its side chain or a copolymer comprising the novel fluorine-containing ethylenic monomer having fluoroalkyl carbonyl group as an essential component.

In the fluorine-containing polymer of the present invention, the structural unit M of the fluorine-containing ethylenic monomer having fluoroalkyl carbonyl group is selected from the fluorine-containing ethylenic monomers of the above-mentioned formulae (14) to (25) and examples thereof are the same as the monomers mentioned above.

In the fluorine-containing polymer of the present invention, the structural unit A1 is an optional component and is not limited particularly as far as it is a monomer copolymerizable with the structural unit M1. The structural unit A1 may be optionally selected depending on intended applications and required characteristics of the is fluorine-containing polymer.

Examples of the structural unit A1 are, for instance, the structural units to ⑤ explained in the second of the present invention.

In the fluorine-containing polymer of the present invention, various combinations and proportions of the structural units M1 and A1 can be selected from the above-mentioned examples depending on intended applications, physical properties (particularly glass transition temperature, hardness, etc.), functions (transparency and refractive index) and the like.

The fluorine-containing polymer of the present invention contains the structural unit M1 as an essential component and has functions due to the structural unit M1 itself such as maintaining a low refractive index and imparting transparency to the polymer, functions due to carbonyl group such as imparting solubility in a solvent, adhesion to a substrate and crosslinkability, and functions due to hemi-acetal after acid hydrolysis such as solubility in a solvent, adhesion to a substrate, crosslinkability and solubility in an aqueous alkaline solution (including a developing solution). Therefore even if the fluorine-containing polymer of the present invention contains a larger amount of the structural unit M1 or in the extreme case, even if the polymer consists of the structural unit M1 (100% by mole), transparency and the refractive index can be maintained.

Also in the case of the copolymer of the present invention comprising the structural unit M1 and the structural unit A1 of the copolymerizable monomer, when the structural unit A1 is selected from the above-mentioned examples, the polymer having a higher hardness (high glass transition temperature), a low refractive index and a high transparency can be obtained.

In the copolymer comprising the structural unit M1 and the structural unit A1, the proportion of the structural unit M1 may be not less than 0.1% by mole based on the whole monomers constituting the fluorine-containing polymer. The proportion is not less than 2.0% by mole, preferably not less than 5% by mole, more preferably not less than 10% by mole in order to obtain the cured article having a high hardness, excellent abrasion resistance and scratch resistance and good chemical resistance and solvent resistance by curing (crosslinking).

In order to impart solubility in an alkaline solution and solubility in water to the fluorine-containing polymer of the present invention, it is preferable that the structural unit M1 is contained in an amount of not less than 10% by mole, preferably not less than 20% by mole, more preferably not less than 30% by mole.

The fluorine-containing polymer of the present invention is preferable particularly for the resist applications since neither a refractive index is increased nor transparency is lowered even if the proportion of the structural unit M1 is increased.

Also in the case of the above-mentioned applications requiring transparency, preferred combinations and proportions of the structural units M1 and A1 are those which can make the fluorine-containing polymer non-crystalline.

The molecular weight of the fluorine-containing polymer of the present invention can be selected, for example, in a range of from 500 to 1,000,000 in number average molecular weight. Preferred molecular weight is from 1,000 to 500,000, particularly from 2,000 to 200,000.

When the molecular weight is too low, mechanical properties are apt to be insufficient, and particularly the cured article and cured coating film become fragile and are apt to be insufficient in strength. If the molecular weight is too high, solubility in a solvent is lowered, and film forming property and leveling property tend to be lowered particularly at forming a thin coating film. For coating applications, most preferable number average molecular weight is selected in a range of from 5,000 to 100,000.

In the fluorine-containing polymer of the present invention, though various refractive indices can be selected depending on kind and content of the structural unit M1 and kind of the structural unit A1 to be copolymerized as case demands, the refractive index of the fluorine-containing polymer itself (before curing) is preferably not more than 1.45, more preferably not more than 1.40, particularly preferably not more than 1.38.

With respect to transparency, it is preferable that the polymer is transparent in the case of vacuum ultraviolet light having a wavelength of not more than 200 nm. For example, an absorption coefficient at 157 nm is not more than 4.0 $\mu m^{-1}$, preferably not more than 3.0 $\mu m^{-1}$, particularly preferably not more than 2.0 $\mu m^{-1}$. Such a polymer is preferable as a base polymer for a $F_2$ resist.

Also it is preferable that the fluorine-containing polymer of the present invention is soluble in general-purpose solvents, for example, in at least one of ketone solvents, acetic acid ester solvents, alcohol solvents, aromatic solvents, glycol ether solvents and glycol ester solvents or in solvent mixtures containing at least one of the above-mentioned general-purpose solvents.

The fluorine-containing polymer of the present invention can be obtained by (co)polymerizing, through known method, the ethylenic monomer having fluoroalkyl carbonyl group which corresponds to the structural unit M1 with the monomer as a copolymerizable component when used for the structural unit A1. For the polymerization, radical polymerization method, anion polymerization method, cation polymerization method and the like can be employed. Among them, the radical polymerization method is preferably used from the point that each monomer exemplified to obtain the polymer having fluoroalkyl carbonyl group of the present invention has good radial polymerizability, control of composition and molecular weight is easy and production in an industrial scale is easy.

In order to initiate the radical polymerization, means for initiation is not limited particularly as far as the polymerization proceeds radically. The polymerization is initiated, for example, with an organic or inorganic radical polymerization initiator, heat, light, ionizing radiation or the like. The polymerization can be carried out by solution polymerization, bulk polymerization, suspension polymerization, emulsion polymerization or the like. The molecular weight is controlled by the contents of monomers to be used for the polymerization, the content of polymerization initiator, the content of chain transfer agent, temperature, etc. The components of the copolymer can be controlled by the starting monomer components.

Further the present inventors have found that the fluorine-containing polymer obtained by polymerizing a specific monomer among fluorine-containing ethylenic monomers having hydroxyl (OH) is dissolved well in an alkaline developing solution which is used in a developing step of a photoresist process.

Also the present inventors have found that the composition comprising the above-mentioned fluorine-containing polymer or the fluorine-containing polymer having protected OH group and a photoacid generator is useful as a photoresist composition.

Namely, the fourth of the present invention is the photoresist composition which is a composition comprising:

(A) a fluorine-containing polymer having, as an essential component, a structural unit obtained by polymerizing a fluorine-containing ethylenic monomer having OH group, (B) a photoacid generator, and (C) a solvent, in which, when the carbon atom bonded to OH group of the fluorine-containing ethylenic monomer having OH group is named the first carbon atom and a structure consisting of the first carbon atom up to the neighboring fourth carbon atom is assumed to be a model structure, the fluorine-containing ethylenic monomer having OH group satisfies Equation 1:

$$\Delta H = H(M-O^-) + 200 - H(M-OH) \leq 75 \qquad \text{(Equation 1)}$$

and more preferably satisfies Equation 2:

$$\Delta H = H(M-O^-) + 200 - H(M-OH) \leq 70 \qquad \text{(Equation 2)}$$

wherein H(M—OH) is a produced enthalpy of the model structure, H(M—O$^-$) is a produced enthalpy of the fluorine-containing ethylenic monomer after dissociation of the OH group and a produced enthalpy of hydrogen ion is assumed to be a constant of 200 kJ/mol.

Generally it has been said that with respect to a relation between acidity and solubility in alkali, as the acidity is increased, namely, as an acid dissociation constant pKa is decreased, the solubility in alkali is increased. However it cannot be said that whenever a pKa value is small, solubility in alkali is high. For example, solubility of a resist in a developing solution is not determined only by a pKa value.

Also transparency against laser beam which is used for pattern formation is an important factor for a resist material. From the viewpoint of transparency against a $F_2$ laser, attention is focused on fluorine-containing compounds. However, for example, a pKa value of OH group of phenol which is a representative example of hydrocarbon compounds having OH group is 10 pKa, and solubility thereof in a developing solution is good, but on the other hand, among fluorine-containing polymers obtained by copolymerizing fluorine-containing ethylenic monomers having OH group of which pKa is about 10 similarly, there are polymers not dissolving in a developing solution.

As mentioned above, it has been difficult to select a compound having most suitable solubility in a developing solution only by a pKa value.

The present inventors have made another approach to this matter paying attention to a produced energy before and after acid dissociation of OH group and have found that a fluorine-containing polymer having a structural unit of a fluorine-containing monomer having OH group which satisfies the ΔH (difference in produced energy) defined above by a specific equation has unexpectedly excellent solubility in a developing solution. This equation relating to the ΔH was first found by the present inventors.

In the fluorine-containing ethylenic monomer having OH group, a proportional relation between ΔH defined above and a pKa value can be recognized in a wide range of pKa value, and more definite proportional relation is established particularly at the pKa value of 12 or lower. However such a proportional relation cannot be recognized in the case of hydrocarbon alcohols and the like though the reason for that is not clear.

Based on those new findings, further studies have been made, and it was found that a fluorine-containing polymer obtained by polymerizing a fluorine-containing ethylenic monomer having OH group which satisfies the above-mentioned equation of ΔH or the fluorine-containing polymer having a functional group of protected OH group is excellent in solubility in a developing solution while maintaining excellent transparency.

Next, a method of calculating a difference ΔH in produced energy before and after acid dissociation in the present invention is explained below.

Provided that the carbon atom bonded to OH group of the fluorine-containing ethylenic monomer having OH group is the first carbon atom, attention is paid only to the neighboring carbon atoms and the carbon atom adjacent to the first carbon atom is assumed to be the second carbon atom and the carbon atom adjacent to the second carbon atom is assumed to be the third carbon atom. A structure up to the third or the fourth carbon atom is selected. If an atomic valence on the third or the fourth carbon atom is insufficient, a structure subjected to replacement with hydrogen atom is assumed to be the model structure.

The reason why the structure up to the fourth carbon atom at maximum is assumed to be the model structure is that even if a structure including the fifth or more carbon atoms which are far from OH is considered, it does not have an effect greatly on the ΔH value, and for comparing ΔH, the structure up to the fourth carbon atom suffices. Also in case of a large model structure or a model structure having a large fluorine content, there arises a problem that a sufficient accuracy is difficult to obtain by a software of calculation method of molecular orbital available on the market, which is not preferable.

If technical problems of the calculation are solved, the ΔH value of the whole fluorine-containing ethylenic monomer may be calculated without using the model structure.

If the number of fluorine atoms in the structure increases, an accuracy of MOPAC calculation (explained infra) is lowered. Therefore when the number of fluorine atoms in the model structure up to the fourth carbon is seven or more, it is preferable to calculate using a model structure up to the third carbon.

For example, in the case of a fluorine-containing ethylenic monomer having OH group which is represented by the formula:

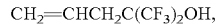

when the carbon atoms are numbered, the monomer is represented by:

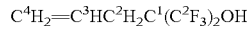

and the structure including carbon atoms up to the fourth carbon atom ($C^4$) and having six or less fluorine atoms can be used for the calculation. Therefore the whole molecular structure $CH_2$=$CHCH_2C(CF_3)_2OH$ is used for the calculation.

Also in the case of the following fluorine-containing ethylenic monomer:

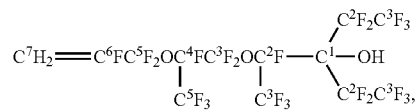

when carbon atoms up to the fourth carbon atom ($C^4$) are used, the number of fluorine atoms are not less than seven. Therefore the model structure up to the third carbon atom ($C^3$), namely:

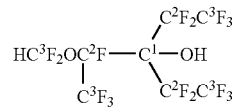

is used for the calculation.

Then the calculation of molecular orbital of the adopted model structure is carried out to calculate a produced enthalpy: H(M—OH) before the acid dissociation.

Each produced enthalpy is calculated using the semiempirical calculation method of molecular orbital: AMI method (described in M. J. S. Dewar, E. G. Zoebisch, E. F. Heary and J. J. P. Stewart, Journal of American Chemical Society, 107, p3902 (1985)). In the present invention, the calculation is carried out using MOPAC calculation software MOPAC97 (software for calculation of molecular orbital) available from FUJITSU LIMITED which uses CS Chem3D (R) Version 4.0 available from Cambridge Soft Corporation.

With respect to the same model structure in which OH has been dissociated, a produced enthalpy H(M—O⁻) after the acid dissociation is calculated by the same method as above. The produced enthalpy of hydrogen ion is set at 200 kJ/mol as a constant.

The ΔH values of the respective fluorine-containing ethylenic monomers having OH group are determined unambiguously by the above-mentioned calculation.

The fluorine-containing polymer (A) for the photoresist composition of the present invention contains the structural unit obtained by polymerizing a fluorine-containing ethylenic monomer having OH group which has a ΔH value of not more than 75 kJ/mol calculated by the above-mentioned calculation method. The polymer is preferable as a photoresist being excellent in transparency and high in solubility in an aqueous solution of 2.38% by weight of tetramethyl ammonium hydroxide (developing solution) though it has been said that fluorine-containing polymers are difficult to be dissolved in such a solution.

Further preferred fluorine-containing polymer (A) of the photoresist composition of the present invention is one derived from a monomer having the ΔH value of preferably not more than 70 kJ/mol, more preferably not more than 50 kJ/mol. When the ΔH value is too large, solubility in a developing solution of the polymer obtained by polymerization becomes insufficient, and at forming a resist pattern, a sufficient resolution is not obtained, a fine pattern is not obtained and scum and residue easily remain in the resist.

In the photoresist composition of the present invention, another preferable embodiment of the fluorine-containing polymer (A) is a polymer containing, as an essential component, a structural unit obtained by polymerizing a fluorine-containing ethylenic monomer having a structure represented by the formula (50):

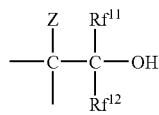
(50)

wherein $Rf^{11}$ and $Rf^{12}$ are the same or different and each is a perfluoroalkyl group having 1 to 20 carbon atoms; Z is fluorine atom or a perfluoroalkyl group having 1 to 20 carbon atoms.

The present inventors have found that not only by an effect of $Rf^{11}$ and $Rf^{12}$ but also by an effect of the group Z bonded to carbon atom adjacent to carbon atom bonded to $Rf^{11}$ and $Rf^{12}$, the polymer exhibits good solubility in an aqueous solution of 2.38% by weight of tetramethyl ammonium hydroxide (developing solution) and is preferred as a polymer for a resist.

In the structure of the formula (50), examples of preferred $Rf^{11}$ and $Rf^{12}$ are the same as the examples of $Rf^1$ and $Rf^2$ of the novel fluorine-containing monomers (formulae (1) to (6)) having OH group explained supra.

In the structure of the formula (50), Z is selected from fluorine atom or a perfluoroalkyl group having 1 to 20 carbon atoms. Examples of the preferred perfluoroalkyl group are the same as the examples of $Rf^1$. Particularly preferred are F, $CF_3$ and $C_2F_5$. In one molecule of the fluorine-containing ethylenic monomer which is an essential component constituting the fluorine-containing polymer (A) may be present at least one structure of the formula (50), and two or more structures of the formula (50) may be present in one molecule.

Though the ΔH value of the fluorine-containing ethylenic polymer having the structure of the formula (50) may exceed 75 kJ/mol, it is preferable that many structural units having the ΔH value of not more than 75 kJ/mol are contained in the polymer. As a matter of course, the ΔH value of the polymer is preferably not more than 75 kJ/mol, more preferably not more than 70 kJ/mol, particularly preferably not more than 50 kJ/mol.

In the resist composition of the present invention, the fluorine-containing ethylenic monomer having OH group which is used for the fluorine-containing polymer (A) is preferably a fluorine-containing ethylenic monomer represented by the formula (51):

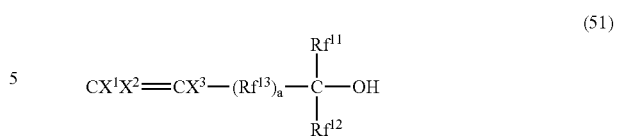
(51)

wherein $X^1$ and $X^2$ are the same or different and each is H or F; $X^3$ is H, F, Cl or $CF_3$; $Rf^{11}$ and $Rf^{12}$ are the same or different and each is a perfluoroalkyl group having 1 to 20 carbon atoms; $Rf^{13}$ is a fluorine-containing alkylene group having 1 to 40 carbon atoms or a fluorine-containing alkylene group having ether bond which has 1 to 100 carbon atoms and the sum of carbon atom and oxygen atom of two or more; a is 0 or 1. It is particularly preferable that the monomer of the formula (51) is a fluorine-containing ethylenic monomer represented by the formula (52):

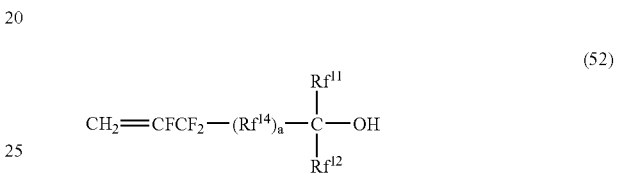
(52)

wherein $Rf^{11}$, $Rf^{12}$ and a are as defined in the formula (51); $Rf^{14}$ is a fluorine-containing alkylene group having 1 to 39 carbon atoms or a fluorine-containing alkylene group having ether bond which has 1 to 99 carbon atoms and the sum of carbon atom and oxygen atom of two or more, or a fluorine-containing ethylenic monomer represented by the formula (53):

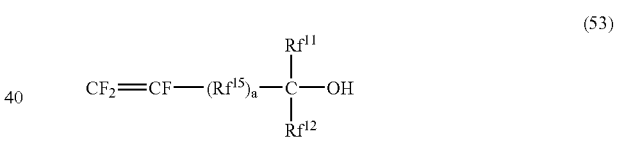
(53)

wherein $Rf^{11}$, $Rf^{12}$ and a are as defined in the formula (51); $Rf^{15}$ is a fluorine-containing alkylene group having 1 to 40 carbon atoms or a fluorine-containing alkylene group having ether bond which has 1 to 100 carbon atoms and the sum of carbon atom and oxygen atom of two or more.

Though the ΔH values of the fluorine-containing ethylenic monomers of the formulae (51), (52) and (53) may exceed 75 kJ/mol, it is preferable that many structural units having the ΔH value of not more than 75 kJ/mol are contained. As a matter of course, the ΔH value of the monomer is preferably not more than 75 kJ/mol, more preferably not more than 70 kJ/mol, particularly preferably not more than 50 kJ/mol.

Particularly preferred are the fluorine-containing ethylenic monomers having OH group of the formulae (51), (52) and (53) which have the structure of the formula (50).

In the fluorine-containing ethylenic monomers having OH group of the formulae (51) to (53) which are used for the fluorine-containing polymer (A) of the resist composition of the present invention, examples of the preferred $Rf^{11}$ and $Rf^{12}$ are the same as those of the $Rf^1$ and $Rf^2$ of the above-mentioned novel fluorine-containing ethylenic monomers having OH group (formulae (1) to (6)).

In the fluorine-containing ethylenic monomers having OH group of the formulae (51) to (53), examples of the preferred $Rf^{13}$, $Rf^{14}$ and $Rf^{15}$ (in the case of a=1) are the same as those of the $Rf^3$, $Rf^4$ and $Rf^5$ of the above-mentioned novel fluorine-containing ethylenic monomers having OH group (formulae (1) to (3)), respectively.

Examples of the preferred fluorine-containing ethylenic monomers having OH group of the formulae (51) to (53) are the same as in the above-mentioned novel fluorine-containing ethylenic monomers having OH group of the formulae (4), (5) and (6).

Examples of the more preferred fluorine-containing ethylenic monomers having OH group of the formulae (51) to (53) are the same as the examples of the above-mentioned novel fluorine-containing ethylenic monomers having OH group (formulae (1) to (6)).

In the resist composition of the present invention, the fluorine-containing polymer (A) is a polymer having the structural unit derived from the above-mentioned fluorine-containing ethylenic monomer having OH group and is preferably a fluorine-containing polymer having a number average molecular weight of from 500 to 1,000,000 which is represented by the formula (60):

$$-(M2)-(A2) \qquad (60)$$

wherein M2 is a structural unit derived from at least one fluorine-containing ethylenic monomer selected from the fluorine-containing ethylenic monomers having OH group which satisfy the above-mentioned Equation 1 and Equation 2, the fluorine-containing ethylenic monomers having OH group which have the structure of the formula (50) and/or the fluorine-containing ethylenic monomers having OH group of the formulae (51) to (53), A2 is a structural unit derived from monomer copolymerizable with the structural unit M2, and the structural unit M2 and the structural unit A2 are contained in amounts of from 0 to 100% by mole and from 0 to 99.9% by mole, respectively.

Namely, the polymer is a homopolymer of a specific fluorine-containing ethylenic monomer having OH group or a copolymer comprising, as an essential component, such a fluorine-containing ethylenic monomer having OH group.

The structural unit A2 is an optional component and is not limited particularly as far as it is copolymerizable with the structural unit M2. The structural unit A2 may be optionally selected depending on the intended required characteristics of the fluorine-containing polymer.

Examples of the structural unit A2 are, for instance, the structural units of ① to ⑤ explained in the second of the present invention.

In the fluorine-containing polymer (A) which is used for the photoresist composition of the present invention, various combinations and proportions of the structural units M2 and A2 can be selected from the above-mentioned examples depending on intended applications, physical properties (particularly glass transition temperature, hardness, etc.), functions (transparency and refractive index) and the like.

The fluorine-containing polymer (A) which is used for the photoresist composition of the present invention contains the structural unit M2 as an essential component and has functions due to the structural unit M2 itself such as maintaining a low refractive index and imparting transparency to the polymer and functions due to hydroxyl such as imparting solubility in a solvent, solubility in an aqueous alkaline solution, adhesion to a substrate and crosslinkability. Therefore even if the fluorine-containing polymer of the present invention contains a larger amount of the structural unit M2 or in the extreme case, even if the polymer consists of the structural unit M2 (100% by mole), transparency and a refractive index can be maintained.

Also in the case of the copolymer of the present invention comprising the structural unit M2 and the structural unit A2 of the copolymerizable monomer, when the structural unit A2 is selected from the above-mentioned examples, the fluorine-containing polymer having a higher glass transition temperature, a high transparency (particularly in vacuum ultraviolet region) and a high dry etching resistivity can be obtained.

In the copolymer comprising the structural unit M2 and the structural unit A2, the proportion of the structural unit M2 may be not less than 0.1% by mole based on the whole monomers constituting the fluorine-containing polymer.

In order to impart solubility in an alkaline solution (developing solution) to the fluorine-containing polymer, it is preferable that the structural unit M2 is contained in an amount of not less than 10% by mole, preferably not less than 20% by mole, more preferably not less than 30% by mole.

In the fluorine-containing polymer (A) which is used for the photoresist composition of the present invention, even if the proportion of the structural unit M2 is increased, transparency is not lowered. Namely, the polymer is preferable for resist applications since solubility in a developing solution can be imparted to the polymer efficiently while maintaining transparency thereof.

Also in the case of the above-mentioned applications requiring transparency, preferred combinations and proportions of the structural units M2 and A2 are those which can make the fluorine-containing polymer non-crystalline.

The molecular weight of the fluorine-containing polymer (A) which is used for the photoresist composition of the present invention can be selected, for example, in a range of from 500 to 1,000,000 in number average molecular weight. Preferred molecular weight is from 1,000 to 500,000, particularly from 2,000 to 200,000.

When the molecular weight is too low, mechanical properties are apt to be insufficient, and a resist film is apt to be insufficient in strength. If the molecular weight is too high, solubility in a solvent is lowered and film forming property and leveling property tend to be lowered particularly at forming a thin coating film. For coating applications, most preferable number average molecular weight is selected in a range of from 5,000 to 100,000.

With respect to transparency, it is preferable that the polymer is transparent in vacuum ultraviolet region at a wavelength of not more than 200 nm. For example, an absorption coefficient at 157 nm is not more than 3.0 $\mu m^{-1}$, preferably not more than 2.0 $\mu m^{-}$, particularly preferably not more than 1.0 $\mu m^{-1}$. Such a polymer is preferable as a base polymer for a $F_2$ resist.

Also it is preferable that the fluorine-containing polymer (A) is soluble in general-purpose solvents, for example in at least one of ketone solvents, acetic acid ester solvents, alcohol solvents, aromatic solvents, glycol ether solvents and glycol ester solvents or in solvent mixtures containing at least one of the above-mentioned general-purpose solvents.

The fluorine-containing polymer (A) which is used for the photoresist composition of the present invention can be obtained by (co)polymerizing, through known method, the fluorine-containing ethylenic monomer having OH group which corresponds to the structural unit M2 with the monomer of the structural unit A2 when used as a copolymerizable component. For the polymerization, radical polymerization method, anion polymerization method, cation polymerization method and the like can be employed.

Among them, the radical polymerization method is preferably used from the point that each monomer exemplified to obtain the fluorine-containing polymer having OH group of the present invention has good radial polymerizability, control of composition and molecular weight is easy and production in an industrial scale is easy.

In order to initiate the radical polymerization, means for initiation is not limited particularly as far as the polymerization proceeds radically. The polymerization is initiated, for example, with an organic or inorganic radical polymerization initiator, heat, light, ionizing radiation or the like. The polymerization can be carried out by solution polymerization, bulk polymerization, suspension polymerization, emulsion polymerization or the like. The molecular weight is controlled by the contents of monomers to be used for the polymerization, the content of polymerization initiator, the content of chain transfer agent, temperature, etc. The components of the copolymer can be controlled by the starting monomer components.

Further in the fluorine-containing polymer (A) which is used for the photoresist composition of the present invention, a part or the whole of OH groups may be protected with a protective group which is capable of changing to OH group through a reaction by an acid. The protective group is changed to OH group with an acid generated from the photoacid generator, and thereby the polymer can act as a positive type resist.

Examples of acid-labile groups are:

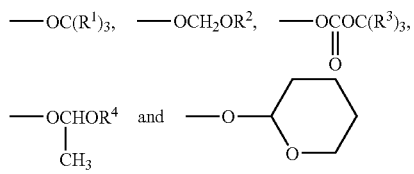

wherein $R^1$, $R^2$, $R^3$ and $R^4$ are the same or different alkyl groups of 1 to 5 carbon atoms.

More concretely there are preferably:

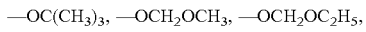

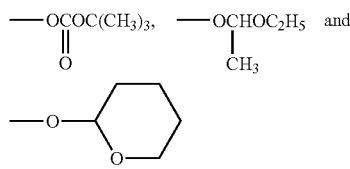

and from the viewpoint of good acid reactivity,

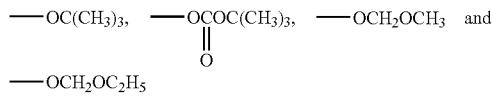

are preferred. Further from the viewpoint of good transparency, —OC(CH$_3$)$_3$, —OCH$_2$OCH$_3$ and —OCH$_2$OC$_2$H$_5$ are preferred.

The fluorine-containing polymer (A) having only OH group can be used as a negative type resist in combination with known crosslinking agent.

Also in case of use for a positive type resist, when OH is present together with another acid-labile group, for example, a functional group which is changed to COOH group due to action of an acid, solubility in a developing solution and a dissolving rate can be adjusted and resolution can be enhanced.

Also the introduction of OH group to the fluorine-containing polymer is preferred since adhesion to a substrate can be improved.

In the photoresist composition of the present invention, the photoacid generator (B) is a compound which generates acid or cation by irradiating the photoacid generator itself or the photoresist composition containing the photoacid generator with radiation. The photoacid generators can be used in a mixture of two or more thereof.

Examples of the preferable photoacid generator are the same as the photoacid generators (B) described in WO01/74916.

Those onium salts having a fluorine-containing alkyl group are preferred since they are high in transparency in vacuum ultraviolet region, and are also preferable from the viewpoint of good compatibility with the fluorine-containing polymer (A) having OH group and/or a functional group protecting the OH group in the photoresist composition of the present invention.

The content of photoacid generator in the photoresist composition of the present invention is preferably from 0.1 to 30 parts by weight, more preferably from 0.2 to 20 parts by weight, most preferably from 0.5 to 10 parts by weight based on 100 parts by weight of the fluorine-containing polymer (A) having OH group and/or a functional group protecting the OH group.

When the content of photoacid generator is less than 0.1 part by weight, sensitivity is lowered, and when the photoacid generator is used in an amount of more than 30 parts by weight, an amount of light to be absorbed by the photoacid generator is increased and a sufficient amount of light does not reach a substrate and therefore resolution is apt to be lowered.

Also to the photoresist composition of the present invention may be added an organic base capable of acting, as a base, on an acid generated from the above-mentioned photoacid generator.

The purpose of adding the organic base is to prevent migration of the acid generated from the photoacid generator and to prevent a resist pattern from undergoing a dimensional change during an interval between the exposure and the PEB (post exposure bake) treatment. Therefore the organic base is not limited particularly as far as it is a compound capable of neutralizing the acid generated from the photoacid generator as mentioned above. The organic base is preferred because when an inorganic compound is used as a base, a very small amount of residue thereof remains after forming a pattern and eliminating the resist, and has an adverse effect on the pattern formation. The organic base is an organic amine compound selected from nitrogen-containing compounds. Examples thereof are pyrimidine compounds such as pyrimidine, 2-aminopyrimidine, 4-aminopyrimidine, 5-aminopyrimidine, 2,4-diaminopyrimidine, 2,5-diaminopyrimidine, 4,5-diaminopyrimidine, 4,6-diaminopyrimidine, 2,4,5-triaminopyrimidine, 2,4,6-triaminopyrimidine, 4,5,6-triaminopyrimidine, 2,4,5,6-tetraaminopyrimidine, 2-hydroxypyrimidine, 4-hydroxypyrimidine, 5-hydroxypyrimidine, 2,4-dihydroxypyrimidine, 2,5-dihydroxypyrimidine, 4,5-dihydroxypyrimidine, 4,6-dihydroxypyrimidine, 2,4,5-trihydroxypyrimidine, 2,4,6-trihydroxypyrimidine, 4,5,6-trihydroxypyrimidine, 2,4,5,6-tetrahydroxypyrimidine, 2-amino-4-hydroxypyrimidine, 2-amino-5-hydroxypyrimidine, 2-amino-4,5-dihydroxypyrimidine, 2-amino-4,6-dihydroxypyrimidine, 4-amino-2,5-dihydroxypyrimidine, 4-amino-2,6-dihydroxypyrimidine, 2-amino-4-methylpyrimidine, 2-amino-5-methylpyrimidine, 2-amino-4,5-dimethylpyrimidine, 2-amino-4,6-dimethylpyrimidine, 4-amino-2,5-dimethylpyrimidine, 4-amino-2,6-dimethylpyrimidine, 2-amino-4-methoxypyrimidine, 2-amino-5-methoxypyrimidine, 2-amino-4,5-dimethoxypyrimidine, 2-amino-4,6-dimethoxypyrimidine, 4-amino-2,5-dimethoxypyrimidine, 4-amino-2,6-dimethoxypyrimidine, 2-hydroxy-4-methylpyrimidine, 2-hydroxy-5-methylpyrimidine, 2-hydroxy-4,5-dimethylpyrimidine, 2-hydroxy-4,6-dimethylpyrimidine, 4-hydroxy-2,5-dimethylpyrimidine, 4-hydroxy-2,6-dimethylpyrimidine, 2-hydroxy-4-methoxypyrimidine, 2-hydroxy-5-methoxypyrimidine, 2-hydroxy-4,5-dimethoxypyrimidine, 2-hydroxy-4,6-dimethoxypyrimidine, 4-hydroxy-2,5-dimethoxypyrimidine and 4-hydroxy-2,6-dimethoxypyrimidine; pyridine compounds such as pyridine, 4-dimethylaminopyridine and 2,6-dimethylpyridine; amines substituted with hydroxyalkyl group having not less than 1 and not more than 4 of carbon atoms such as diethanolamine, triethanolamine, triisopropanolamine, tris(hydroxymethyl)aminomethane and bis(2-hydroxyethyl)iminotris(hydroxymethyl)methane; aminophenols such as 2-aminophenol, 3-aminophenol and 4-aminophenol and the like. Preferable organic bases are pyrimidines, pyridines or amines having hydroxyl, and particularly preferred are amines having hydroxyl. Those organic bases may be used solely or in a mixture of two or more thereof.

The content of organic base in the photoresist composition of the present invention is preferably from 0.1 to 100% by mole, more preferably from 1 to 50% by mole based on the content of photoacid generator. When the content of organic base is less than 0.1% by mole, resolution is low, and when the content of organic base is more than 100% by mole, sensitivity tends to be lowered.

In the photoresist composition of the present invention, when a negative photoresist composition is prepared using the fluorine-containing polymer (A) having OH group, a crosslinking agent may be used as case demands as mentioned above.

The crosslinking agent is not limited particularly and can be optionally selected from crosslinking agents which have been usually used for negative photoresist compositions.

Examples of preferable crosslinking agent are, for instance, N-methylol melamine compounds, N-alkoxymethylol melamine compounds, urea compounds, epoxy compounds, isocyanate compounds and the like.

Those crosslinking agents may be used solely or in combination of two or more thereof. Among them, a combination of the melamine resin and the urea resin is advantageous.

The content of crosslinking agent in the photoresist (particularly negative type) composition of the present invention is from 3 to 70 parts by weight, preferably from 5 to 50 parts by weight, more preferably from 10 to 40 parts by weight based on 100 parts by weight of the fluorine-containing polymer (A) having OH group and/or a functional group protecting the OH group. When the content is less than 3 parts by weight, a resist pattern is difficult to be formed. The content of more than 70 parts by weight is not preferred because light transmittance is lowered, resolution is easily lowered and developing property is lowered.

The photoresist composition of the present invention may contain, as case demands, various additives which have been usually used in this field, such as a dissolution inhibitor, sensitizer, dye, adhesion betterment material and water retention agent. While the presence of water is necessary for generating an acid in the photoresist composition, the acid can be generated effectively in the presence of a small amount of water retention agent such as polypropylene glycol.

When those additives are used, a total amount thereof is up to about 20% by weight based on the weight of the whole solids in the composition.

In the photoresist composition of the present invention, the solvent (C) is one which is capable of dissolving the fluorine-containing polymer (A) having OH group and/or a functional group protecting the OH group, the photoacid generator (B) and the above-exemplified various additives. The solvent is not limited particularly as far as good coatability (surface smoothness, uniformity of coating thickness, etc.) can be obtained.

Examples of the preferable solvent (C) are, for instance, cellosolve solvents such as methyl cellosolve, ethyl cellosolve, methyl cellosolve acetate and ethyl cellosolve acetate; ester solvents such as diethyl oxalate, ethyl pyruvate, ethyl-2-hydroxybutyrate, ethyl acetoacetate, butyl acetate, amyl acetate, ethyl butyrate, butyl butyrate, methyl lactate, ethyl lactate, methyl 3-methoxypropionate, ethyl 3-methoxypropionate, methyl 2-hydroxyisobutyrate and ethyl 2-hydroxyisobutyrate; propylene glycol solvents such as propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate and dipropylene glycol dimethyl ether; ketone solvents such as 2-hexanone, cyclohexanone, methyl amino ketone and 2-heptanone; aromatic hydrocarbons such as toluene, xylene, chlorobenzene and chlorotoluene; a solvent mixture of two or more thereof and the like.

Also in order to enhance solubility of the fluorine-containing polymer (A), a fluorine-containing solvent may be used as case demands.

Examples thereof are, for instance, $CH_3CCl_2F$ (HCFC-141b), a mixture of $CF_3CF_2CHCl_2$ and $CClF_2CF_2CHCl$ (HCFC-225), perfluorohexane, perfluoro(2-butyltetrahydrofuran), methoxy-nonafluorobutane, 1,3-bistrifluoromethylbenzene, and in addition, fluorine-containing alcohols such as:

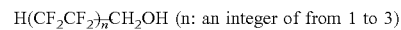

$H(CF_2CF_2)_nCH_2OH$ (n: an integer of from 1 to 3)

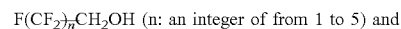

$F(CF_2)_nCH_2OH$ (n: an integer of from 1 to 5) and

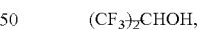

$(CF_3)_2CHOH$, benzotrifluoride, perfluorobenzene, perfluoro(tributylamine), $ClCF_2CFClCF_2CFCl_2$ and the like.

Those fluorine-containing solvents may be used solely, in a mixture of two or more thereof or in a mixture of one or more of the fluorine-containing solvents and non-fluorine-containing solvents.

The amount of the solvent (C) is selected depending on kind of solids to be dissolved, kind of a substrate to be coated, an intended coating thickness, etc. From the viewpoint of easiness of coating, it is preferable that the solvent is used in such an amount that the concentration of the whole solids of the resist composition becomes from 0.5 to 70% by weight, preferably from 1 to 50% by weight, particularly preferably from 5 to 30% by weight.

The photoresist composition of the present invention is subjected to resist pattern formation according to conventional photoresist technology. In order to form a pattern properly, first, a solution of the photoresist composition is applied on a substrate such as a silicon wafer by a spinner or the like, and is dried to form a photosensitive layer. A pattern is drawn by irradiating the layer with ultraviolet ray, deep-UV, excimer laser or X-ray by a reduction projection exposure system or the like through a proper mask pattern or the pattern is drawn with an electron beam, and then heating afterwards. The layer is then subjected to developing treatment with a developing solution, for example, an aqueous alkali solution such as an aqueous solution of 1 to 10% by weight of tetramethyl ammonium hydroxide. Thus an image faithful to the mask pattern can be obtained by this pattern forming method.

It has been found that by using the photoresist composition of the present invention, a resist film (photosensitive layer) having a high transparency even in vacuum ultraviolet region could be formed. Therefore the photoresist composition of the present invention can be preferably used particularly for a photolithography process using a $F_2$ laser (wavelength of 157 nm) which is under development aiming at a technology node of 0.1 μm.

The present invention is then explained below by means of examples, but is not limited to them.

In the following Examples, Preparation Examples and Comparative Examples, equipment and measuring conditions used for evaluation of physical properties are as follows.

(1) NMR: available from BRUKER CO., LTD.
Measuring conditions of $^1$H-NMR: 300 MHz (tetramethylsilane=0 ppm)
Measuring conditions of $^{19}$F-NMR: 300 MHz (trichlorofluoromethane=0 ppm)

(2) IR analysis: Measuring is carried out at room temperature with a Fourier-transform infrared spectrophotometer available from Perkin Elmer Co., Ltd.

(3) GPC: A number average molecular weight is calculated from data measured by gel permeation chromatography (GPC) by using GPC HLC-8020 available from Toso Kabushiki Kaisha and columns available from Sodex Co., Ltd. (one GPC KF-801, one GPC KF-802 and two GPC KF-806M were connected in series) and flowing tetrahydrofuran (THF) as a solvent at a flowing rate of 1 ml/minute.

(4) GC-Mass: Measurement is carried out by using QP1000 available from Shimadzu Corporation. Detection is carried out by an impact ionization method at an ionization energy of 70 eV.

(5) Glass transition temperature by DSC: Measurement is carried out by increasing a temperature to 150° C. at a temperature increasing rate of 10° C./min and measuring Tg in 2nd run.

EXAMPLE 1

A 500 ml four-necked glass flask equipped with a reflux condenser, dropping funnel, thermometer, stirrer and cooling device was charged with 22.5 g of ethyl 9,9-dihydro-2,5-bistrifluoromethyl-3,6-dioxa-8-nonenoate (compound of the formula (18)):

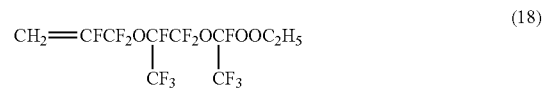

49.2 g of perfluoroethyl iodide and 200 ml of diethyl ether and was cooled to −78° C.

While maintaining the flask at that temperature, 110 ml of a solution of 1 mole/liter methyllithium (a solution of diethyl ether) was added dropwise slowly over six hours through the dropping funnel. After completion of the addition, stirring was continued at 0° C. for two hours and the mixture was poured into about 1 liter of 1% diluted hydrochloric acid solution.

An organic layer was extracted with ether. Then the ether layer was washed with water and dried with anhydrous magnesium sulfate, followed by eliminating anhydrous magnesium sulfate and distilling off ether. The obtained reaction mixture was subjected to column chromatography using a silica gel as a stationary phase (mobile phase: hexane/ethyl acetate=10/1), and 20.0 g of a fluorine-containing ethylenic monomer having hydroxyl of 97% purity which is represented by the formula (19) was isolated (yield: 62%).

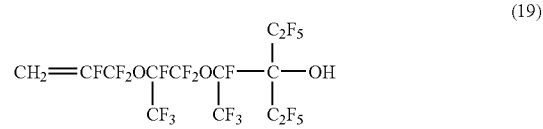

$^{19}$F-NMR analysis (ppm): −146.1

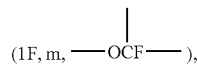

−138.2

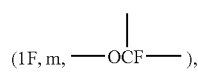

−123.0 (1F, m, C=CF),
−119.4 to −121.7 (4F, m, —CF$_2$—), −82.4 (3F, s, —CF$_3$)—, 81.1 (3F, s, CF$_3$), −77.4 to −80.4 (8F, m, —CF$_3$, OCF$_2$)—, 74.0 (2F, m, C=C—CF$_2$) IR analysis (A): 1693 ($v_{c=c}$)

EXAMPLE 2

A 100 ml four-necked glass flask equipped with a reflux condenser, thermometer and stirrer was charged with 10 g of the fluorine-containing ethylenic monomer having hydroxyl of the formula (19) obtained in Example 1 and 1.3 g of 8% perfluorohexane solution of fluorine-containing peroxide represented by the formula (20):

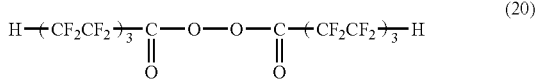

(20)

and while cooling with dry ice/methanol bath, purging with nitrogen gas and evacuation were repeated to eliminate dissolved oxygen in the solution. Polymerization was carried out at 20° C. for 24 hours with stirring and a solid having a high viscosity was obtained.

The solid was dissolved in acetone and then poured into hexane, followed by re-precipitation for refining and then vacuum drying to obtain 5.9 g of a fluorine-containing polymer.

According to $^{19}$F-NMR and IR analyses, the obtained fluorine-containing polymer was found to be a homopolymer of the fluorine-containing ethylenic monomer having hydroxyl of the formula (19).

A molecular weight of the polymer measured by GPC analysis was 3,000 of Mn and 3,700 of Mw, and a glass transition temperature thereof measured by DSC analysis was −26° C.

The obtained fluorine-containing polymer was soluble in acetone, THF, pentafluorodichloropropane (HCFC-225) and 2.36 N aqueous solution of tetramethyl ammonium hydroxide.

EXAMPLE 3

A 500 ml four-necked glass flask equipped with a reflux condenser, dropping funnel, thermometer, stirrer and cooling device was charged with 22.5 g of ethyl 9,9-dihydro-2,5-bistrifluoromethyl-3,6-dioxa-8-nonenoate (compound of the formula (18)), 49.2 g of perfluoroethyl iodide and 200 ml of diethyl ether and was cooled to −78° C.

While maintaining the flask at that temperature, 110 ml of a solution of 1 mole/liter methyllithium (a solution of diethyl ether) was added dropwise slowly over six hours through the dropping funnel. After completion of the addition, stirring was continued at 0° C. for two hours and the mixture was poured into about 1 liter of saturated ammonium chloride solution.

An organic layer was extracted with ether. Then the ether layer was washed with water and dried with anhydrous magnesium sulfate, followed by eliminating anhydrous magnesium sulfate and distilling off ether. The obtained reaction mixture was subjected to column chromatography using a silica gel as a stationary phase (mobile phase: hexane/ethyl acetate=25/1) and 15.0 g of a fluorine-containing monomer having perfluoroethylcarbonyl group of 98% purity which is represented by the formula (31) was isolated (yield: 57%).

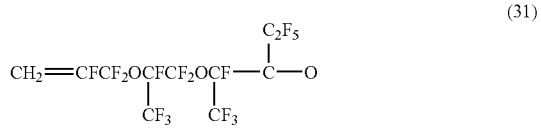

(31)

$^{19}$F-NMR (CDCl$_3$): δ −74.0 (2F, m, OCF$_3$), −77.5 to −80.0 (2F, m, OCF$_3$), −79.8 (3F, s, CF$_3$), −81.1 (3F, s, CF$_3$), −82.4 (3F, s, CF$_3$), −120.6 (2F, m, CF$_2$CF$_3$), −123.1 (1F, m, CH$_2$=CF), −138.2 (1F, m, OCFC=O), −146.1 (1F, m, OCFCF$_2$), $^1$H-NMR (CDCl$_3$): δ 5.15 to 5.35 (2H, m, CH$_2$=CF), IR analysis (cm$^{-1}$): 1790 (v$_{c=c}$), 1695 (v$_{c=c}$)

EXAMPLE 4

(Synthesis of CH$_2$=CFC(CF$_3$)$_2$OH)

A 1-liter three-necked flask equipped with a thermometer, cooling tube and dropping funnel was charged with 102 g (1.11 moles) of αfluoroacrylic acid fluoride, 10 g of cesium fluoride and 179 g of potassium fluoride and was cooled in ice bath in nitrogen gas atmosphere. While maintaining the temperature inside the flask at 3° to 10° C., 386 g (2.7 moles) of CF$_3$Si(CH$_3$)$_3$ was added dropwise into the flask over two hours. The inside temperature was raised to room temperature and stirring was carried out overnight. The reaction solution was poured into ice water and subjected to extraction with diethyl ether.

After washing an organic layer with water, diluted hydrochloric acid and sodium bicarbonate solution, the organic layer was dried with calcium chloride, followed by distillation for refining to obtain 23.7 g of 1,1-bistrifluoromethyl-2-fluoro-2-propene-1-ol (yield: 70%).

Boiling point: 56° C. $^1$H-NMR (solvent: CDCl$_3$): 5.27 (1H, dd), 5.17(1H, dd), 4.18(1H, s) $^{19}$F-NMR (solvent: CDCl$_3$): −76.7(6F, d), −113.4(1F, m) MS: 212(M$^+$), 195, 173, 153, 143, 123, 73, 69, 45, 31

PREPARATION EXAMPLE 1

(Synthesis of CF$_2$=CFC(CF$_3$)$_2$OH)

After the inside of a 1-liter flask was evacuated and replaced with nitrogen gas, a still was charged with zinc powder (115 g, 1.76 moles) and dehydrated DMF (400 ml) and a dropping funnel was charged with CF$_3$CFBr$_2$ (208 g, 0.8 mole) and dehydrated DMF (100 ml), followed by heating and stirring in nitrogen gas atmosphere. After adding dropwise over two hours while maintaining the flask temperature at 80° to 90° C., heating and stirring were carried out at 90° to 95° C. for 4.5 hours.

Dimroth condenser was changed to a dry ice/acetone condenser, and while cooling the still, CF$_3$COCF$_3$ was introduced in a gaseous form at room temperature. The introduction of CF$_3$COCF$_3$ was terminated at the time when it was observed that the refluxing did not stop and the reaction was not advanced. An amount of introduced CF$_3$COCF$_3$ was 92 g (0.55 mole). Then after un-reacted CF$_3$COCF$_3$ was removed by heating and evacuating, ether was added and an organic layer was washed with 1N hydrochloric acid and dried with CaCl$_2$.

As a result of refining by rectification with a rectifying column containing a filler therein, 56.6 g of a solution comprising 48.6% of 1,1-bistrifluoromethyl-2,3,3-trifluoro-2-propene-1-ol: CF$_2$=CFC(CF$_3$)$_2$OH and 47.0% of ether in GC area ratio was obtained.

$^{19}$F-NMR (solvent: CDCl$_3$): −77.0 (6F, q), −91.6 (1F, dd), −106.8 (1F, m), −184.1 (1F, m) MS: 248 (M$^+$), 209, 181, 179, 159, 109, 69(CF$_3$), 31(CF)

EXPERIMENTAL EXAMPLE 1

(Calculation of ΔH of Various Fluorine-containing Ethylenic Monomers Having OH Group)

With respect to various fluorine-containing ethylenic monomers having OH group shown in Table 1, calculation of molecular orbital was carried out by the above-mentioned MOPAC97, AM1 method to calculate a produced enthalpy H(M—OH) before acid dissociation and a produced enthalpy H(M—O⁻) after acid dissociation. The calculation of monomers having a long chain was carried out using a model structure shown in Table 1. Then provided that a produced enthalpy of hydrogen ion is a constant of 200 kJ/mol, each produced enthalpy H was substituted in the following Equation 3:

$$\Delta H = H(M—O^-) + 200 - H(M—OH) \quad \text{(Equation 3)}$$

to obtain ΔH (kJ/mol). The results are shown in Table 1.

EXPERIMENTAL EXAMPLE 2

(Measurement of pKa of Various Fluorine-containing Ethylenic Monomers Having OH Group)

(1) Measurement of pKa of $CH_2=CHCH_2C(CF_3)_2OH$

In a solution of water/acetone of 10/15 ml was put 0.7865 g of $CH_2=CHCH_2C(CF_3)_2OH$, followed by stirring at room temperature. After it was confirmed that the solution became homogeneous, titration was carried out with a 0.2 mol/liter NaOH solution. A titration curve was obtained by adding a NaOH solution dropwise in increments of 0.15 ml and recording a pH value at every addition. An equivalence point was determined by an inflection point (maximum differential value of titration curve=dpH/dml) of the titration curve. In this case, the equivalence point was 14.5 ml. A pH value at 7.25 ml which is a half of the equivalence point was read from the titration curve and was found to be 10.98. From a titration curve of water/acetone solution and aqueous solution which had been measured previously as a blank solution, a difference in a pH value derived from an electric potential difference between the solutions at titration of 7.25 ml was 1.29. Therefore from 10.98−1.29=9.69, a pKa value of $CH_2=CHCH_2C(CF_3)_2OH$ was determined as 9.69.

In case of titration of 1.0865 g of $CH_2=CHCH_2C(CF_3)_2$ OH by the same procedures as above, an equivalence point was 20.15 ml and a half of equivalence point was 10.08 ml. A pH value at a half of the equivalence point was 10.78. A difference in a pH value between the both solutions at 10.08 ml was 1.14, and from 10.78−1.14=9.64, a pKa value of $CH_2=CHCH_2C(CF_3)_2OH$ was determined as 9.64.

When the same procedures as above were carried out except that about 0.05 mol/liter NaOH solution was used as a titration solution, an equivalence point of 0.115 g of $CH_2=CHCH_2C(CF_3)_2OH$ was 8.00 ml and a half of equivalence point was 4.00 ml. A pH value at this time was 10.92. A difference in a pH value between the both solutions at 4.00 ml was 1.38, and from 10.92−1.38=9.54, a pKa value of $CH_2=CHCH_2C(CF_3)_2OH$ was determined as 9.54.

From those experiments carried out three times, a pKa value of $CH_2=CHCH_2C(CF_3)_2OH$ was determined as 9.6.

With respect to the various fluorine-containing ethylenic monomers having OH group shown in Table 1, a pKa value was measured by the same procedures as above. The results are shown in Table 1.

PREPARATION EXAMPLE 2

(Synthesis of Fluorine-containing Allyl Ether Homopolymer Having OH Group)

A 100 ml glass flask equipped with a stirrer was charged with 20.4 g of perfluoro-(1,1,1,9,9-tetrahydro-2,5-bistrifluoromethyl-3,6-dioxanonenol) of the following formula (41):

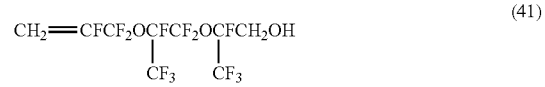

and 8.6 g of perfluorohexane solution of 8.0% by weight of $[H(CF_2CF_2)_3—COO—]_2$. After the inside of the flask was sufficiently replaced with nitrogen gas, the mixture was stirred at 20° C. for 24 hours in nitrogen gas stream, and a solid having a high viscosity was produced.

The obtained solid was dissolved in diethyl ether and poured into perfluorohexane, followed by separation and drying to obtain 18.6 g of a colorless transparent polymer. As a result of ¹⁹F-NMR and IR analyses, the obtained polymer was a fluorine-containing polymer having OH group at an end of its side chain and consisting of the structural unit of the above-mentioned fluorine-containing allyl ether. According to GPC analysis using tetrahydrofuran (THF) as a solvent, a number average molecular weight thereof was 21,000.

PREPARATION EXAMPLE 3

A 100 ml stainless steel autoclave equipped with a pressure gauge, valve and thermometer was charged with 5.2 g of $CH_2=CHCH_2C(CF_3)_2OH$, 50 ml of HCFC-141b and 0.3 g of bis(4-tert-butylcyclohexyl)peroxydicarbonate (TCP), and while cooling with dry ice/methanol solution, the inside of a system was sufficiently replaced with nitrogen gas, Then 10.0 g of tetrafluoroethylene was introduced, followed by a reaction while shaking at 40° C. for 20 hours.

After removing un-reacted monomer, a polymer solution was subjected to re-precipitation with hexane to separate a copolymer. Vacuum drying was carried out until a constant weight was reached and 4.0 g of a copolymer was obtained.

As a result of ¹⁹F-NMR analysis, components of the copolymer was TFE and $CH_2=CHCH_2C(CF_3)_2OH$ in a ratio of 42:58% by mole.

A number average molecular weight thereof was 21,000 according to GPC analysis.

EXAMPLE 5

Polymerization and isolation and refining of a polymer were carried out in the same manner as in Preparation Example 3 except that 5.3 g of $CH_2=CFC(CF_3)_2OH$ obtained in Example 4 was used instead of $CH_2=CHCH_2C(CF_3)_2OH$.

As a result of ¹⁹F-NMR analysis, components of the copolymer was TFE and $CH_2=CFC(CF_3)_2OH$ in a ratio of 57:43% by mole.

A number average molecular weight thereof was 5,500 according to GPC analysis.

EXPERIMENTAL EXAMPLE 3

(Evaluation of Solubility in Developing Solution)

(1) Coating

10% butyl acetate solutions of the fluorine-containing polymers obtained in Example 2 and Preparation Examples 2 to 4 were prepared and were coated on a Si substrate with a spin coater so that a coating thickness became 200 nm, and then drying was carried out.

(2) Evaluation of Solubility

The dried Si substrate was dipped in a 2.38% aqueous solution of tetramethyl ammonium hydroxide for 60 seconds. The substrate was then taken out and dried at room temperature. Whether or not there remained a film without being dissolved was checked with naked eyes.

When there remains no film, solubility is evaluated as ○. The results are shown in Table 1.

This compound was subjected to GC-Mass, $^{19}$F-NMR and $^{1}$H-NMR analyses and the above-mentioned structure was determined.

EXAMPLE 6

Polymerization was carried out in the same manner as in Example 2 except that 3.2 g of:

TABLE 1

| Fluorine-containing ethylenic monomer having OH | Model structure | Monomer | ΔH Exp. Ex. 1 | Measured pKa Exp. Ex. 2 | Solubility of polymer in a developing solution Exp. Ex. 3 |
|---|---|---|---|---|---|
| CH$_2$=CFCF$_2$OCFCF$_2$OCFCOH (with CF$_3$, CF$_3$, C$_2$F$_5$, C$_2$F$_5$ substituents) | HCF$_2$OCFCOH (with CF$_3$, C$_2$F$_5$, C$_2$F$_5$ substituents) | Ex. 1 | −15.8 | 6.8 | ○ (Ex. 2) |
| CH$_2$CFCF$_2$OCFCF$_2$OCFCH$_2$OH (with CF$_3$, CF$_3$ substituents) | HCF$_2$OCFCH$_2$OH (with CF$_3$ substituent) | — | 122.3 | 12.6 | X (not dissolved) (Prep. Ex. 2) |
| CH$_2$=CFC(CF$_3$)$_2$OH | — | Ex. 4 | 38.7 | 8.0 | ○ (Ex. 5) |
| CF$_2$=CFC(CF$_3$)$_2$OH | — | Prep. Ex. 1 | 10.5 | 7.1 | — |
| CH$_2$CHCH$_2$C(CF$_3$)$_2$OH | — | — | 76.2 | 9.6 | Δ (a residue found) |

PREPARATION EXAMPLE 4

(Introduction of Protective Group)

A 100 ml four-necked flask equipped with a reflux condenser, thermometer, stirrer and dropping funnel was charged with 3.5 g of sodium hydride (60% purity) and 10 ml of tetrahydrofuran. While maintaining the inside temperature of the flask at 5° to 10° C., 56 g of the fluorine-containing allyl ether having —C(C$_2$F$_5$)$_2$OH group of the formula (19) prepared in Example 1 was added dropwise over one hour. After completion of the addition, stirring was carried out at room temperature for 1.5 hours. Then 9.6 g of chloromethyl ethyl ether (ClCH$_2$OC$_2$H$_5$) was added dropwise over one hour. After completion of the addition, stirring was carried out at room temperature for 5 hours. After completion of the reaction, water was added thereto and an organic substance was extracted with ether. The ether layer was washed with saturated NaHCO$_3$ solution and then dried with anhydrous magnesium sulfate. After the drying, ether was distilled off, and by distillation under reduced pressure, 53 g of a compound of the following formula (42):

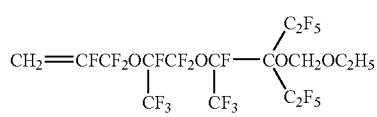

(42)

was obtained.

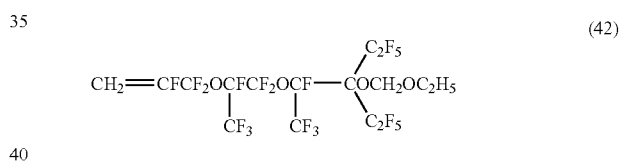

(42)

and 6.8 g of the fluorine-containing ethylenic monomer having OH group of the formula (19):

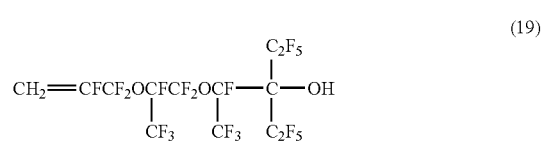

(19)

were used instead of a single use of the fluorine-containing ethylenic monomer having OH group of the formula (19) obtained in Example 1. Thereby a solid having a high viscosity was obtained. This solid was dissolved in acetone and then poured in hexane, followed by re-precipitation, refining and vacuum-drying to obtain 5.7 g of a fluorine-containing polymer.

As a result of $^{19}$F-NMR and IR analyses, the obtained fluorine-containing polymer was a copolymer comprising the monomer of the formula (19) and the monomer of the formula (22) in a ratio of 70:30% by mole. Molecular weights Mn and Mw thereof were 3,000 and 3,700, respectively according to GPC analysis.

EXPERIMENTAL EXAMPLE 4

(Measurement of Transparency at a Wavelength of 157 nm)

(1) Preparation of Coating Composition

The fluorine-containing polymers obtained in Examples 2 and 6 were dissolved in butyl acetate so that the concentration thereof became 3%, respectively. Thus coating compositions were prepared.

(2) Coating

① Coating on a Substrate ($MgF_2$) for Measuring Transparency

Each coating composition was applied on a $MgF_2$ substrate at room temperature with a spin coater under the condition of 1,000 rpm. After the coating, the coating composition was baked at 100° C. for 15 minutes to form transparent coating films.

② Measurement of Coating Thickness

Coating films were formed by applying the respective coating compositions under the same conditions as above except that a silicon wafer was used instead of the $MgF_2$ substrate. The coating thickness was measured with a AFM device (SPI3800 available from SEIKO DENSHI KABUSHIKI KAISHA).

(3) Measurement of Transparency in Vacuum Ultraviolet Region

① Measuring Device

Setani-Namioka type spectrometer (BL-7B available from HIGH ENERGY KENKYU KIKO)

Slit: 7/8—7/8

Detector: PMT

Grating (GII: Blaze wavelength 160 nm, 1,200 gratings/mm)

For an optical system, refer to Rev. Sic. Instrum., 60(7), 1917 (1989) by H. Namba, et al.

② Measurement of Transmitting Spectrum

A transmitting spectrum at a wavelength of 200 to 100 nm in a coating film formed by applying each coating composition on the $MgF_2$ substrate by the method of (2) ① was measured using the above-mentioned device. Further a molecular absorption coefficient was calculated from the transmittance at 157 nm and the coating thickness.

As a result, an absorption coefficient at 157 nm of the polymer of Example 2 was 0.17 $\mu m^{-1}$ and an absorption coefficient at 157 nm of the polymer of Example 6 was 0.28 $\mu m^{-1}$.

EXPERIMENTAL EXAMPLE 5

(Preparation of Coating Composition and Measurement of Transparency at 157 nm in Vacuum Ultraviolet Region)

(1) Preparation of Coating Composition

To the respective fluorine-containing polymers (A) of Examples 2 and 6 were mixed the photoacid generator (B) in an amount of 5% by weight based on the polymer and the mixture was dissolved in butyl acetate as the solvent (C) so that the polymer concentration became 5% by weight. Then the solution was filtrated with a 0.5 $\mu m$ PTFE membrane filter.

As the photoacid generator, s-(trifluoromethyl)-dibenzothiopheniumtrifluoromethane sulfonate was used.

(2) Coating (3) Measurement of Transparency in Vacuum Ultraviolet Region

Coating and measurement of transparency in vacuum ultraviolet region were carried out in the same manner as in Experimental Example 4 and a molecular absorption coefficient of the resist coating film at 157 nm was calculated.

As a result, an absorption coefficient of the resist coating film obtained from the polymer of Example 2 was 0.45 $\mu m^{-1}$ and an absorption coefficient of the resist coating film obtained from the polymer of Example 6 was 0.58 $\mu m^{-1}$.

EXPERIMENTAL EXAMPLE 6

(Determination of Acid Reactivity)

In 50 ml of 0.1N HCl solution was dipped 1.0 g of the fluorine-containing allyl ether copolymer having —$OCH_2OC_2H_5$ obtained in Example 6, at 50° C. for one hour. The polymer was removed and was dried at 60° C. for one hour. Then with respect to the above polymer dipped in hydrochloric acid solution and the polymer of Example 5 which was not dipped in hydrochloric acid solution, solubility thereof in a developing solution was determined in the same manner as in Experimental Example 3.

The polymer of Example 6 itself was insoluble in a developing solution, but the same polymer dipped in HCl solution was dissolved completely in an alkaline solution.

According to the present invention, there can be provided a novel fluorine-containing ethylenic monomer having hydroxyl or fluoroalkyl carbonyl group which has good polymerizability, particularly radical polymerizability and further a novel fluorine-containing polymer obtained by polymerizing the monomer. The fluorine-containing polymer has excellent optical characteristics and is useful as a base polymer for an antireflection film and a resist.

What is claimed is:

1. A fluorine-containing ethylenic monomer having hydroxyl represented by the formula (1a):

$$CX^1X^2 = CX^3 - (Rf^3)_a - \underset{Rf^2}{\overset{Rf^1}{\underset{|}{\overset{|}{C}}}} - OH \qquad (1a)$$

wherein $X^1$ and $X^2$ are the same or different and each is H or F; $X^3$ is H, F, Cl or $CF_3$ (at least one of $X^1$, $X^2$ and $X^3$ is H and $X^1$, $X^2$ and $X^3$ are not H at the same time); $Rf^1$ and $Rf^2$ are the same or different and each is a perfluoroalkyl group having 1 to 20 carbon atoms; $Rf^3$ is a fluorine-containing alkylene group having 1 to 40 carbon atoms or a fluorine-containing alkylene group having ether bond which has 1 to 100 carbon atoms and the sum of carbon atom and oxygen atom of two or more; a is 1.

2. A fluorine-containing ethylenic monomer having hydroxyl represented by the formula (2):

$$CH_2 = CFCF_2 - (Rf^4)_a - \underset{Rf^2}{\overset{Rf^1}{\underset{|}{\overset{|}{C}}}} - OH \qquad (2)$$

wherein $Rf^1$ and $Rf^2$ are the same or different and each is a perfluoroalkyl group having 1 to 20 carbon atoms; $Rf^4$ is a fluorine-containing alkylene group having 1 to 39 carbon atoms or a fluorine-containing alkylene group having ether bond which has 1 to 99 carbon atoms and the sum of carbon atom and oxygen atom of two or more; a is 0 or 1.

3. A fluorine-containing ethylenic monomer having hydroxyl represented by the formula (3):

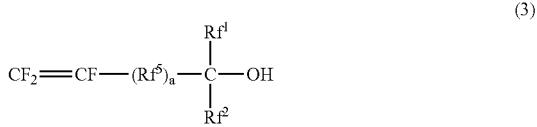
(3)

wherein $Rf^1$ and $Rf^2$ are the same or different and each is a perfluoroalkyl group having 1 to 20 carbon atoms; $Rf^5$ is a fluorine-containing alkylene group having 1 to 40 carbon atoms or a fluorine-containing alkylene group having ether bond which has 1 to 100 carbon atoms and the sum of carbon atom and oxygen atom of two or more; a is 1.

4. A fluorine-containing ethylenic monomer having hydroxyl represented by the formula (5):

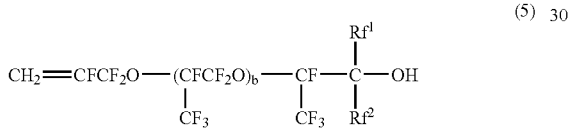
(5)

wherein $Rf^1$ and $Rf^2$ are the same or different and each is a perfluoroalkyl group having 1 to 20 carbon atoms; b is an integer of from 1 to 13.

5. A fluorine-containing polymer having a number average molecular weight of from 500 to 1,000,000 represented by the formula (7a):

-(M)-(A)-      (7a)

wherein the structural unit M is a structural unit derived from the fluorine-containing ethylenic monomer having hydroxyl of claim 1 which is represented by the formula (1a), the structural unit A is a structural unit derived from monomer copolymerizable with the structural unit M, and the structural unit M and the structural unit A are contained in amounts of from 0.1 to 100% by mole and from 0 to 99.9% by mole, respectively.

6. A fluorine-containing polymer having a number average molecular weight of from 500 to 1,000,000 represented by the formula (7b):

-(M)-(A)-      (7b)

wherein the structural unit M is a structural unit derived from the fluorine-containing ethylenic monomer having hydroxyl of claim 3 which is represented by the formula (3), the structural unit A is a structural unit derived from monomer copolymerizable with the structural unit M, and the structural unit M and the structural unit A are contained in amounts of from 0.1 to 100% by mole and from 0 to 99.9% by mole, respectively.

7. A fluorine-containing polymer having a number average molecular weight of from 500 to 1,000,000 represented by the formula (7):

-(M)-(A)-      (7)

wherein the structural unit M is a structural unit derived from a fluorine-containing ethylenic monomer having hydroxyl represented by the formula (1):

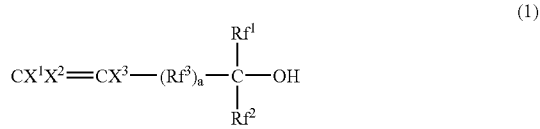
(1)

wherein $X^1$ and $X^2$ are the same or different and each is H or F; $X^3$ is H, F, Cl or $CF_3$; $Rf^1$ and $Rf^2$ are the same or different and each is a perfluoroalkyl group having 1 to 20 carbon atoms; $Rf^3$ is a fluorine-containing alkylene group having 1 to 40 carbon atoms or a fluorine-containing alkylene group having ether bond which has 1 to 100 carbon atoms and the sum of carbon atom and oxygen atom of two or more; a is 1, the structural unit A is a structural unit derived from a fluorine-containing ethylenic monomer copolymerizable with the structural unit M except the monomer of the formula (1), and the structural unit M and the structural unit A are contained in amounts of from 0.1 to 100% by mole and from 0 to 99.9% by mole, respectively.

8. The fluorine-containing polymer of claim 7, wherein the structural unit A is at least one selected from fluorine-containing ethylenic monomers represented by the formula (8):

$CX^4X^5=CX^6X^7$      (8)

wherein $X^4$ and $X^5$ are the same or different and each is H or F; $X^6$ is H, F or $CF_3$; $X^7$ is H, F, Cl or $CF_3$; at least one of $X^4$, $X^5$, $X^6$ and $X^7$ is F or $CF_3$.

* * * * *